(12) United States Patent
Gibson et al.

(10) Patent No.: US 6,537,268 B1
(45) Date of Patent: Mar. 25, 2003

(54) MEDICAL INFUSION DEVICE WITH A SOURCE OF CONTROLLED COMPLIANCE

(75) Inventors: Scott R. Gibson, Granada Hills, CA (US); Peter C. Lord, Valencia, CA (US); Eric M. Lorenzen, Granada Hills, CA (US); Susan M. McConnell, Woodland Hills, CA (US); John F. Gray, Woodland Hills, CA (US); Robert W. Bosley, Cerritos, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 09/335,936

(22) Filed: Jun. 18, 1999

Related U.S. Application Data

(60) Provisional application No. 60/089,719, filed on Jun. 18, 1998.

(51) Int. Cl.[7] .................................................. A61K 9/22
(52) U.S. Cl. ...................................... 604/891.1; 604/93
(58) Field of Search ...................... 604/30, 31, 65–67, 604/891.1, 93.01, 19, 131, 153, 154, 155, 152, 151; 128/DIG. 12, DIG. 13

(56) References Cited

U.S. PATENT DOCUMENTS

| | | | |
|---|---|---|---|
| 4,221,219 A | 9/1980 | Tucker | |
| 4,373,527 A | 2/1983 | Fischell | 128/260 |
| 4,525,165 A | 6/1985 | Fischell | 604/131 |
| 4,594,058 A | 6/1986 | Fischell | 417/413 |
| 4,655,765 A | * 4/1987 | Swift | 604/891 |
| 4,692,147 A | * 9/1987 | Duggan | 604/93 |
| 5,049,141 A | 9/1991 | Olive | 604/891.1 |
| 5,281,210 A | 1/1994 | Burke et al. | 604/891.1 |
| 5,752,930 A | * 5/1998 | Rise et al. | 604/53 |
| 5,797,733 A | 8/1998 | Falk et al. | 417/416 |
| 6,146,325 A | * 11/2000 | Lewis et al. | 600/16 |

FOREIGN PATENT DOCUMENTS

EP          0 687 475          11/1999

* cited by examiner

*Primary Examiner*—Manuel Mendez
(74) *Attorney, Agent, or Firm*—Foley & Lardner

(57) ABSTRACT

Embodiments of medical infusion pumps are provided that include structural elements for providing sources of compliance within a fluid path within the pump. Some preferred embodiments provide implantable infusion pumps with compliance positioned between an exit port of a pumping mechanism and an outlet (e.g. an opening in a catheter) of the infusion pump. Other embodiments provide compliance in fluid path in proximity to entrance port of the pumping mechanism. Insertion of compliance in a flow path that is down stream of the pumping mechanism may aid in minimizing negative effects associated with attempting to force fluid through a restricted flow path that is further downstream, such as that offered by a catheter or other outlet component. Insertion of compliance before the pumping mechanism may aid in reducing negative effects associated with an up stream restricted flow path, such as that which might be offered by a rigid filter located between the reservoir and the pumping mechanism. Several structural components, assemblies, or configurations may be used as sources of compliance. For example, compressible structures (e.g. pillows, drums) are used within a side port of the infusion pump. The compressible structures may quickly distort to accommodate for a large impulse of fluid into the flow path that can not otherwise be readily dealt with. The compression, in turn, results in a restoring force being exerted that returns the structure substantially to its original volume so as to slowly force fluid from the flow path.

22 Claims, 14 Drawing Sheets

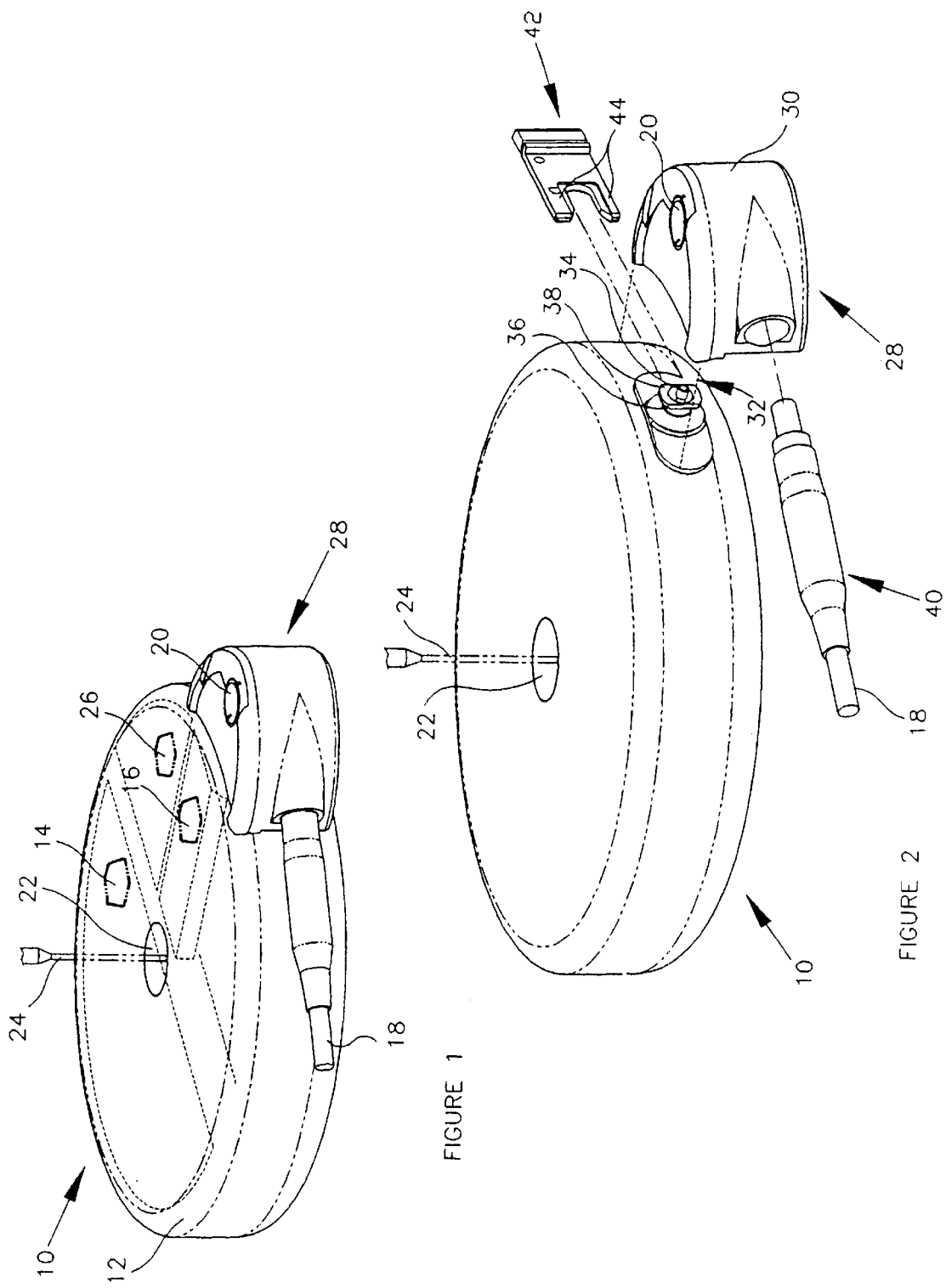

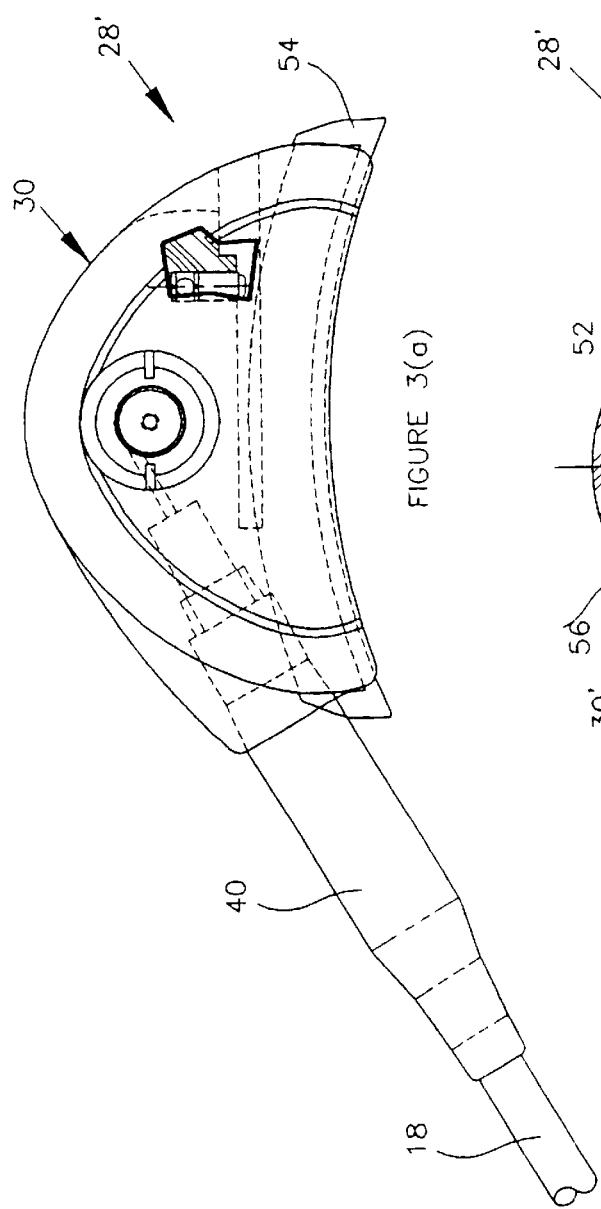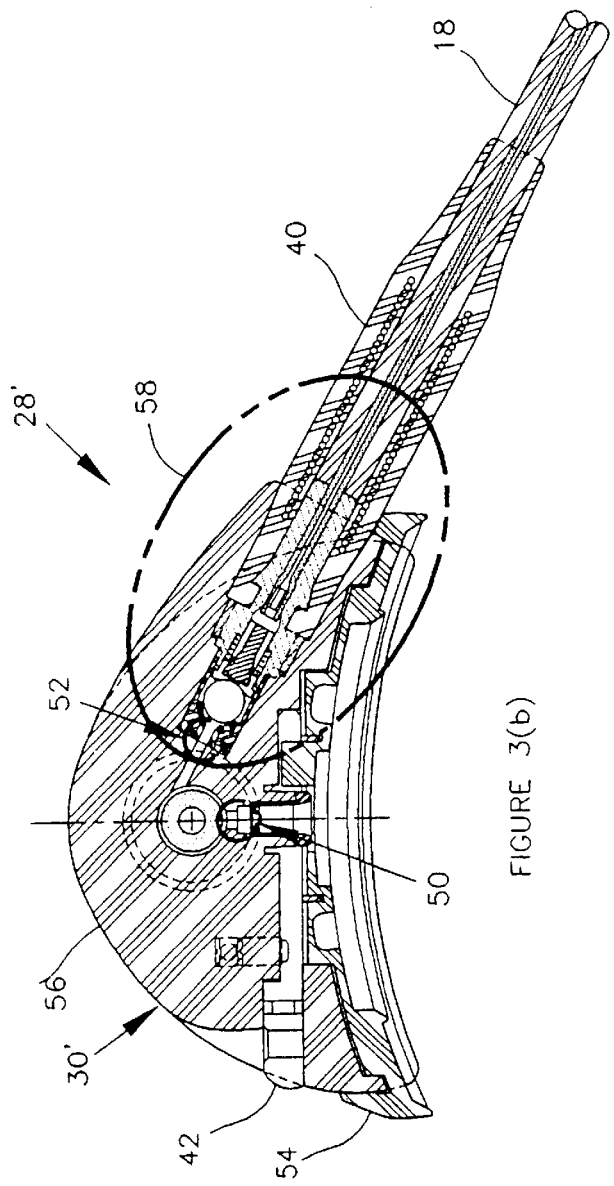
FIGURE 3(a)
FIGURE 3(b)

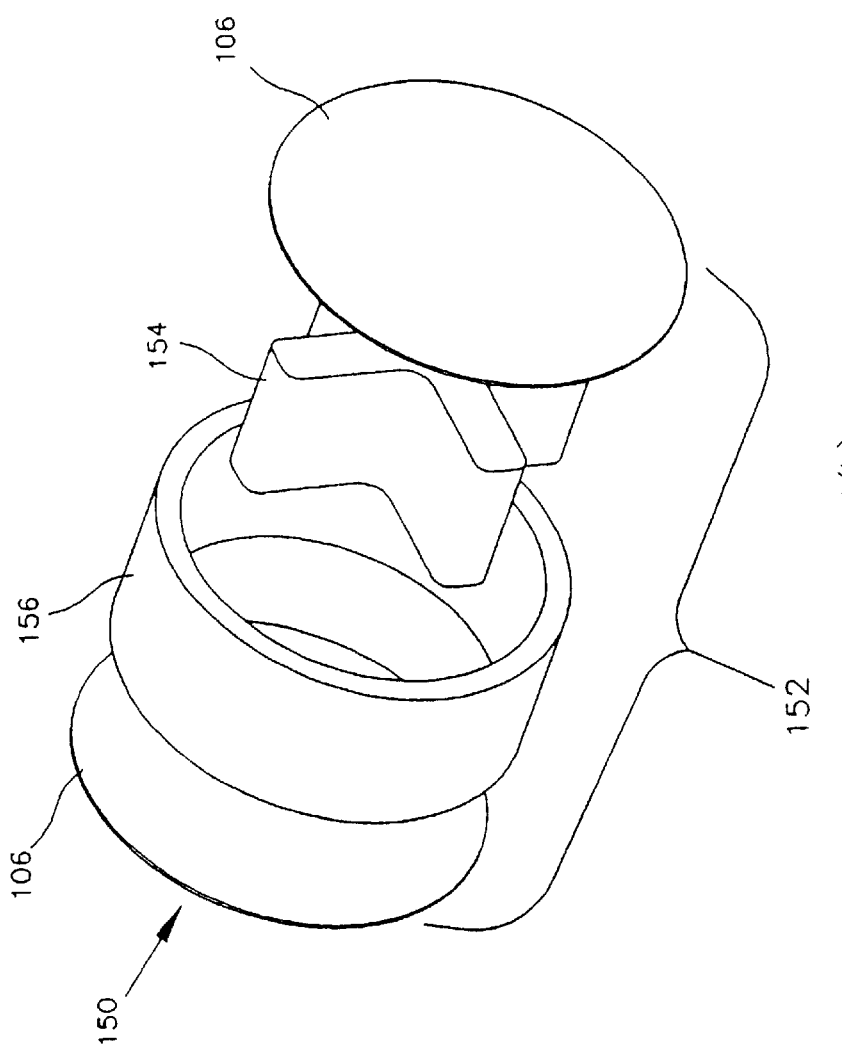
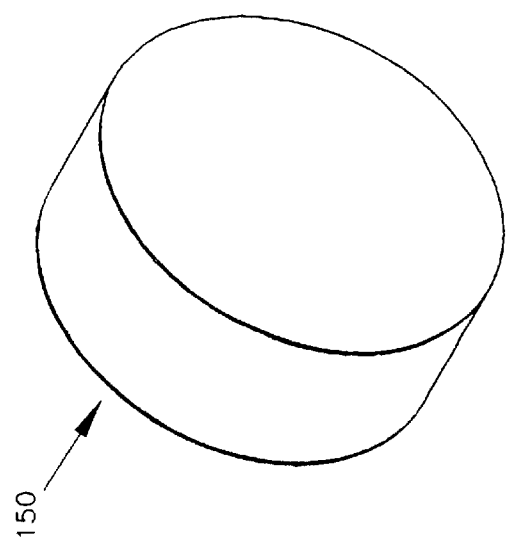
FIGURE 11(b)
FIGURE 11(a)

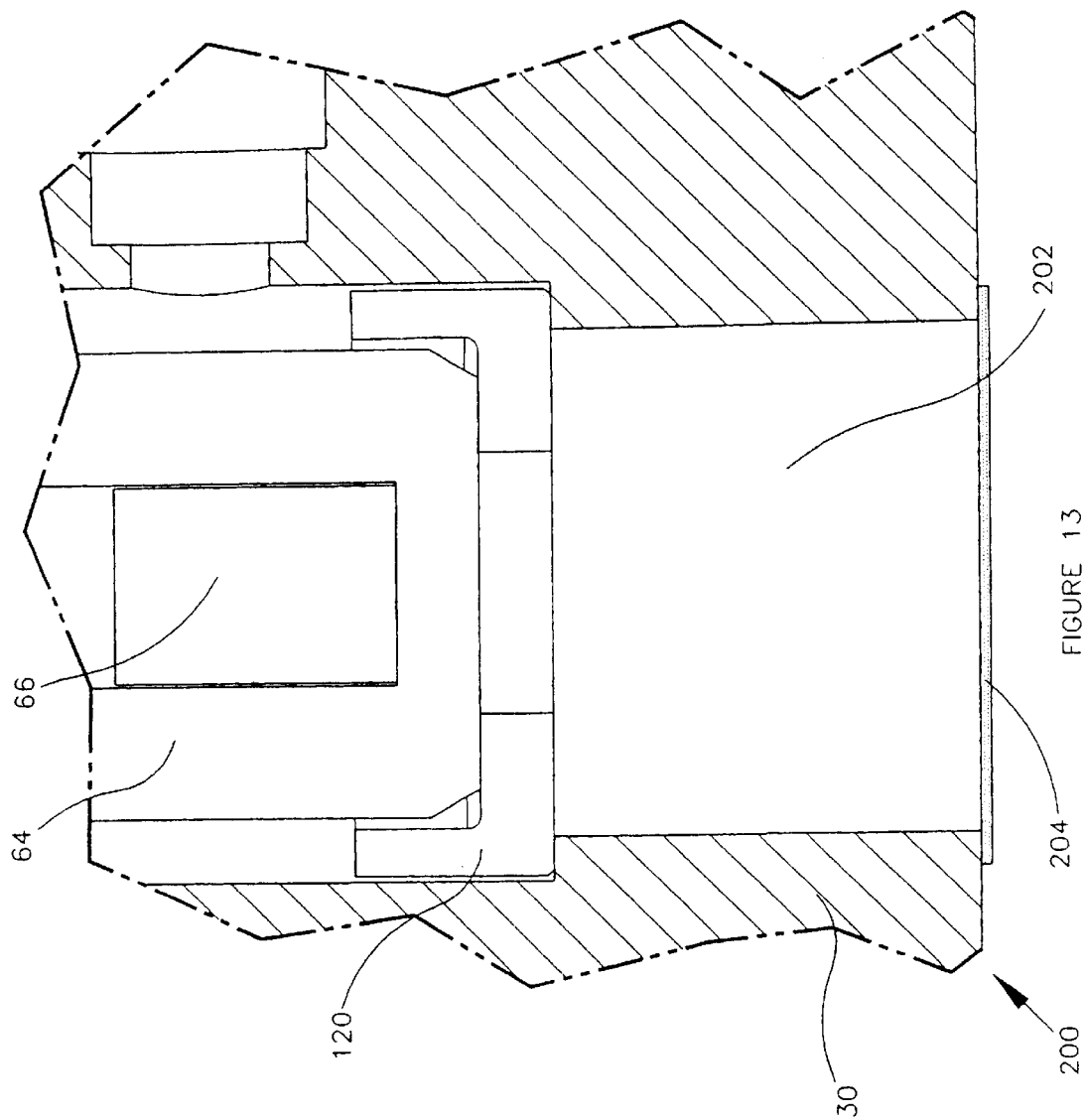

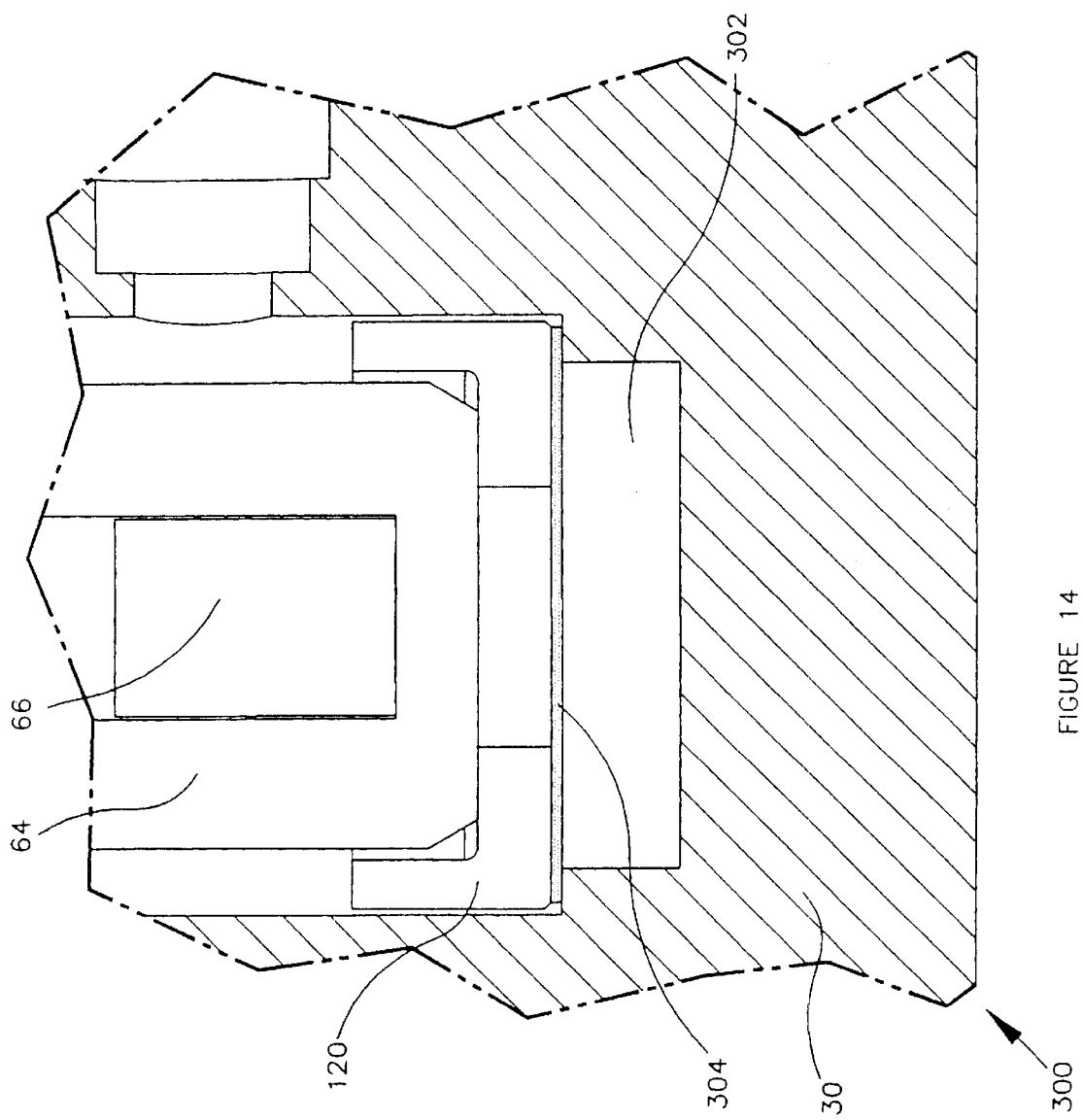

MEDICAL INFUSION DEVICE WITH A SOURCE OF CONTROLLED COMPLIANCE

PRIORITY CLAIM

This application claims priority to U.S. Provisional Application No. 60/089,719, filed Jun. 18, 1998, the full disclosure of which is hereby incorporated by reference as if set forth herein.

FIELD OF THE INVENTION

This invention relates to medical infusion devices that are intended to deliver, in a controlled manner, desired quantities of a fluid to a patient, more particularly this invention relates to the utilization of compliant structures within such medical devices.

BACKGROUND

Both external and internally implanted infusion pumps are generally known in the art for use in delivering a selected fluid to the body of a patient (i.e. body of a person or animal being treated or benefited by the fluid) in a scheduled or preprogrammed manner. Such fluids include drugs, medications, proteins, e.g. insulin, or the like. Programmable medication infusion pumps offer significant potential advantages to patients who are required to comply with a long-term medication treatment regimen. Such pumps can operate automatically, with little or no patient intervention, to administer an important medication such as insulin to a diabetic patient on a regular basis.

Implantable infusion pumps typically include an internal fluid chamber or reservoir for receiving and storing a supply of the selected fluid (e.g. drug, medication, protein such as insulin) a miniature pump mechanism, programmable control means (e.g. electrical circuit possibly including telemetry elements for communication with an external programming device) for operating the pump mechanism to deliver discrete doses of the fluid from the internal reservoir to a desired region within the body. These pumps typically deliver medication to the body through a catheter connected to an output port of the pump mechanism. A refill port is typically provided on the pump to permit transcutaneous needle access for purpose of periodically refilling the pump reservoir with a fresh supply of fluid. Some implantable infusion pumps include a side port that is connected to the output port of the pump mechanism and to a first end of the catheter. The side port may be used in a process of flushing residue from the catheter, flushing the pump, and or to determine pump stroke volume.

Various infusion pumps, associated components and processes, for example, are described in the various patent publications listed in Table 1, the disclosures of which are hereby incorporated herein by reference. The brief description of each publication is provided in Table 1 to aid the reader in finding specific types of teachings. It is not intended that the incorporation of subject matter be limited to those topics specifically indicated, but instead the incorporation is to include all subject matter found in these publications. The teachings in these incorporated publications may be combined with the teachings herein in many ways.

TABLE 1

| Pat. Pub. No. (US if not indicated other wise) Issue Date Inventor(s) | Brief Description of Subject Matter Disclosed in Each Publication |
|---|---|
| 4,373,525 Feb. 15, 1983 Fischell | A change in the internal pressure of the fluid-infusion tube of a peristaltic fluid-infusion pump due to occlusion in the fluid-infusion tube is detected through a change in the diameter of the fluid-infusion tube. The occlusion is detected by detection of the change in the distance between the opposite wall portions of the tube. |
| 4,482,346 Nov. 13, 1984 Reinicke | An integral valve and pumping unit is provided for infusing medication into the body which employs only one moving part. This pumping unit is connected to the medication supply reservoir through a first flow restriction device which has no moving parts but has directional flow characteristics so that liquid medication can flow readily from the reservoir to the pumping unit but flow from the pumping unit to the reservoir encounters a relatively high resistance. A second flow restriction device is connected between the pumping unit and the outlet catheter which is employed to infuse medication into the body, this second flow restriction device likewise having no moving parts and offering relatively little resistance to liquid flow from the pumping unit to the catheter while having relatively high resistance to flow in the opposite direction. The valve portion of the integral valve-pump unit ensures that no liquid can flow either from the reservoir to the catheter or vice versa, when the pumping unit is inoperative or when the reservoir is being filled. |
| 4,486,190 Dec. 4, 1984 Reinicke | The implantable device includes a medication reservoir, a pulsatile pump and an absolute pressure transducer. The pumping pressure wave developed in the pumping chamber is measured by the absolute pressure transducer whose output is used to adjust the pulsing rate of the solenoid operated pump so that the programmed time averaged rate of infusion of medication into the body is precisely maintained throughout all operating temperature and pressure conditions. |
| 4,525,165 Jun. 25, 1985 Fischell | An apparatus for fluid handling and delivery in a medication infusion system is disclosed. The apparatus generally contains a pulsatile pump in combination with at least an accumulation flow restrictor. The pulsatile pump is economical in electrical consumption by virtue of the use of a spring force pumping action. The accumulator flow restrictor smooths the output from the pulsatile pump so that medication is delivered in a manner compatible with human or animal body |

TABLE 1-continued

| Pat. Pub. No. (US if not indicated other wise) Issue Date Inventor(s) | Brief Description of Subject Matter Disclosed in Each Publication |
|---|---|
| | needs. As an example, for infusion of medication such as insulin, the medication infusion system can provide an infusion flow profile which mimics that of insulin production in a normal person. |
| 4,561,443 Dec. 31, 1985 Hogrefe et al. | A two-way coherent inductive communications link between an external transceiver and an internal transceiver located in a biologically implanted programmable medical device. Digitally formatted command data and programming data is transmitted to the implanted medical device by frequency shift keying the inductive communications link. Internal transceiver is powered by the inductive field between internal and external transceivers. Digitally formatted data is transmitted to external transceiver by internal transceiver amplitude modulating inductive field. Immediate verification of the establishment of a reliable communications link is provided by determining existence of frequency lock and bit phase lock between internal and external transceivers. |
| 4,573,994 Mar. 4, 1986 Fischell et al. | Apparatus and method for filling, or refilling, the internal reservoir of a medication infusion system, wherein filling or refilling is permitted only when a means for injecting medication is properly positioned relative to the reservoir. Prior to filling or refilling, a pressure integrity check can be made to help assure that injected medication enters the reservoir without leakage. Additionally, flushing of a portion or all of the medication reservoir can be accomplished if desired. Medication is introduced to and is stored in the reservoir at a pressure below ambient body pressure. |
| 4,604,090 Aug. 5, 1986 Reinicke | An implantable medication infusion device wherein a generally cylindrical manifold is employed having a shallow recess on one face thereof. A flexible diaphragm is positioned to form with the face of said manifold a medication reservoir. A circular cover member is positioned over the diaphragm to form with said diaphragm a pressure stabilizing chamber within which is positioned a two-phase fluid for maintaining a constant pressure on said diaphragm. A permanent magnet is positioned at the center of said diaphragm and is movable therewith. A Hall effect transducer positioned on said manifold opposite said permanent magnet is employed continuously to measure the position of said diaphragm and provide an indication of the amount of medication in said reservoir. A method of filling and sealing the pressure stabilizing chamber which insures that a small bubble of two-phase fluid is present in said chamber at all times. An inlet filter is positioned between the medication reservoir and an inlet check valve to act as a bubble trap during the intake stroke of a pulsatile pumping unit also mounted in the manifold. |
| 4,619,653 Oct. 28, 1996 Fischell | A medication infusion system provides redundant safety and includes condition detecting and informational alarm signal generating apparatus for indicating if (1) a fluid leak occurs in different portions of the system; (2) a programmable input from a patient or physician would result in exceeding a safe dosage limit; (3) the reservoir containing medication has been filled; (4) the intended medication pumping does not correlate with the pumping actually effected; (5) battery voltage is low; (6) the medication reserve is low; and (7) the system has been switched off. The apparatus may provide subcutaneous electrical, thermal, or audible stimulation to the patient and also provides a signal which a physician may monitor. The stimulation may be coded to separately identify each above-listed deviation in nominal system performance. In addition, the number of medication requests are correlated with actual medication dispensing to assure proper operation. An identification scheme is provided which matches the patient with his or her corresponding medication. |
| 4,731,051 Mar. 15, 1988 Fischell et al. | An implantable programmable infusion pump (IPIP) is disclosed and generally includes: a fluid reservoir filled with selected medication; a pump for causing a precise volumetric dosage of medication to be withdrawn from the reservoir and delivered to the appropriate site within the body; and, a control means for actuating the pump in a safe and programmable manner. The control means includes a microprocessor, a permanent memory containing a series of fixed software instructions, and a memory for storing prescription schedules, dosage limits and other data. The microprocessor actuates the pump in accordance with programmable prescription parameters and dosage limits stored in the memory. A communication link allows the control means to be remotely programmed. The control means incorporates a running integral dosage limit and other safety features which prevent an inadvertent or intentional medication overdose. The control means also monitors the pump and fluid handling system and provides an alert if any improper or potentially unsafe operation is detected. |
| 5,514,103 May 7, 1996 Srisathapat et al. | An implantable medication infusion pump is provided of the type having a pressure reservoir with a selected pressure fluid therein for maintaining liquid medication in an adjacent medication chamber under a substantially constant pressure. The reservoir comprises a hollow structural enclosure defined by at least one movable wall and adapted to be filled with a selected quantity of the pressure fluid, particularly such as a selected fluorocarbon in a liquid-vapor state. The movable wall of the pressure reservoir is shared with and defines one side of the medication chamber, with the pressure fluid undergoing appropriate change of state to expand or contract the pressure reservoir in a manner maintaining the |

TABLE 1-continued

| Pat. Pub. No. (US if not indicated other wise) Issue Date Inventor(s) | Brief Description of Subject Matter Disclosed in Each Publication |
|---|---|
| | medication under substantially constant pressure. The improved pressure reservoir includes an internal spacer element to prevent contraction of the pressure reservoir beyond a minimum volume at least slightly greater than the liquid state volume of the pressure fluid therein. With this construction, at least some pressure fluid within the pressure reservoir remains in a vapor state at all times. |
| 5,527,307 Jun. 18, 1996 Srisathapat et al. | A medication infusion pump is provided of the type adapted for implantation into the body of a patient, and for programmable delivery of a selected medication through a catheter to the patient over an extended period of time. A side port assembly is mounted quickly and easily onto the pump and defines a flow path through which the medication is discharged to the catheter. The side port assembly includes an access port to permit transcutaneous needle access to the discharge flow path, in combination with a check valve to prevent backflow within the discharge flow path. The discharge side access port can be used to flush residue from the catheter, or in combination with a primary refill port on the pump to flush the pump and/or to determine actual pump stroke volume. |
| 5,167,633 Dec. 1, 1992 Mann et al. | An improved and simplified pressure reservoir is provided for use with an implantable medication infusion pump to maintain a selected medication in liquid form with a pump housing under a substantially constant pressure. The pressure reservoir comprises a hollow structural enclosure having at least one flexible resilient wall and is adapted to be filled with a selected quantity of a pressure fluid, such as a selected fluorocarbon in a liquid-vapor state, prior to mounting of the reservoir as a structural unit into the infusion pump housing. Within the pump housing, the flexible reservoir wall defines one side of a medication chamber, with the pressure fluid undergoing appropriate change of state to expand or contact the reservoir in a manner maintaining the medication under a substantially constant pressure. The improved reservoir can be provided in a variety of structural shapes and/or utilized in pump housings of various size and shape to permit the pump size to be reduced, or, in the alternative, to increase pump medication capacity without increasing pump housing size. |
| 5,176,644 Jan. 5, 1993 Srisathapat et al. | An implantable medication infusion pump is provided which utilizes an improved and simplified pressure reservoir to maintain a selected medication in liquid form within a pump housing under a substantially constant pressure. The pressure reservoir comprises a hollow structural enclosure having at least one flexible resilient wall and is adapted to be filled with a selected quantity of a pressure fluid, such as a selected fluorocarbon in a liquid-vapor state, prior to mounting of the reservoir as a structural unit into the infusion pump housing. Within the pump housing, the flexible reservoir wall defines one side of a medication chamber, with the pressure fluid undergoing appropriate change of state to expand or contract the reservoir in a manner maintaining the medication under a substantially constant pressure. The improved reservoir can be provided in a variety of structural shapes and/or utilized in pump housings of various size and shape to permit the pump size to be reduced, or, in the alternative, to increase pump medication capacity without increasing pump housing size. |
| 5,197,322 Mar. 30, 1993 Indravudh | An improved process and related apparatus are provided for filling a pressure reservoir of an implantable medication infusion pump with a selected pressure fluid, wherein the pressure reservoir is separated by a movable wall from an adjacent medication chamber. The improved filling process includes vacuum-draw filling of the pressure reservoir with relatively purified pressure fluid in liquid state. The specific quantity of pressure fluid within the pressure reservoir is thereafter calibrated by filling the adjacent medication chamber with a calibration fluid at a predetermined positive pressure, thereby expelling excess pressure fluid from the pressure reservoir. The pressure reservoir is then sealed and the performance characteristics thereof are tested under simulated implantation conditions to confirm the capability of the pressure reservoir to maintain medication within the medication chamber under substantially constant pressure conditions. |
| 5,257,971 Nov. 2, 1993 Lord et al. | A method is provided for reconditioning a medication infusion pump by removal of accumulated medication deposits and the like to restore pump performance without requiring surgical removal of an implanted pump from a patient. The reconditioning process comprises sequential delivery of a buffer solution and a rinse solution to internal pump flow passages. The rinse solution is effective to dissolve medication deposits and the like within narrow pump flow passages before the rinse solution is neutralized by intermixing with the buffer solution. Dissolution of accumulated medication deposits results in restoration of pump performance substantially to original product specifications. |
| 5,328,460 Jul. 12, 1994 Lord et al. | Apparatus located in an implantable medication infusion pump for quickly and easily detecting a condition adversely affecting medication delivery in the implantable medication infusion pump is disclosed which can reliably detect occurrences including an occluded catheter, the presence of air in the pumping mechanism, and the failure of the pumping mechanism. The system uses the amplitude of an acoustic signal generated by operation of the pumping mechanism as compared with a baseline signal to detect an encapsulated or |

TABLE 1-continued

Pat. Pub. No.
(US if not indicated
other wise)
Issue Date
Inventor(s) | Brief Description of Subject Matter Disclosed in Each Publication

| | |
|---|---|
| | occluded catheter or air in the fluid line. In addition, the system can detect a partially encapsulated or occluded catheter by detecting repeated downward slope patterns during repetitive, closely spaced pumping cycles. |
| 5,462,525<br>Oct. 31, 1995<br>Srisathapat et al. | An infusion pump for delivering a selected medication to a patient is provided with an inductance flow sensor for monitoring and verifying delivery of medication in response to pump operation. The flow sensor comprises a compact inductor coil wrapped about a pump discharge conduit, in combination with a magnetically attractable core pin disposed within the discharge conduit for movement to a position within the inductor coil in response to pump outflow. A control circuit operates with minimal power requirements to monitor coil inductance changes as a result of core pin displacement to confirm medication delivery to the patient in response to pump operation. A magnet mounted at one end of the inductor coil draws and retains the core pin at a position retracted from the coil in the absence of pump outflow. |
| 5,466,218<br>Nov. 14, 1995<br>Srisathapat et al. | A medication infusion pump is provided of the type adapted for implantation into the body of a patient, and for programmable delivery of a selected medication through a catheter to the patient over an extended period of time. A side port assembly is mounted quickly and easily onto the pump and defines a flow path through which the medication is discharged to the catheter. The side port assembly includes an access port to permit transcutaneous needle access to the discharge flow path, in combination with a check valve to prevent backflow within the discharge flow path. The discharge side access port can be used to flush residue from the catheter, or in combination with a primary refill port on the pump to flush the pump and/or to determine actual pump stroke volume. |
| 5,785,681<br>Jul. 28, 1998<br>Indravudh | A flow rate controller is provided for regulating the flow rate of medication delivered to a patient by an implantable medication infusion pump of the constant flow type, to minimize or prevent flow rate increases attributable to fluctuations in ambient pressure. The infusion pump comprises an implantable pump housing with a pressurized medication reservoir therein for continuous flow delivery to the patient through a baseline flow path including a restrictor such as a capillary tube. The controller comprises a pressure responsive control valve for connecting a secondary restrictor such as an additional capillary tube in series with the baseline flow path, to prevent undesired increase in the medication flow rate in the event that the patient temporarily encounters a high altitude ambient pressure. |
| 5,797,733<br>Aug. 25, 1998<br>Falk et al. | An electromagnetic pump comprising a housing having fluid receiving and pumping chambers in communication with an inlet and outlet, respectively, an electromagnet carried by the housing external to the fluid chambers thereof, and an armature movable in the housing having a pole portion magnetically attracted by the electromagnet and a piston portion to force fluid out of the chambers and through the pump outlet. A path provides controlled bypass for bubbles in the fluid around the armature piston portion between the fluid pumping chamber and the fluid receiving chamber only during the return stroke of the armature. Fluid inertia is reduced by an outlet orifice in the path of fluid flow from the pump outlet and by a bypass orifice for fluid flow in the bypass path, the orifices being provided either individually or in combination depending upon the fluid flow characteristics of the system including the pump. An accumulator in the fluid flow path between the pump outlet and a catheter leading away from the pump alleviates inertial and viscous effects arising from the catheter. The armature pole portion has a fluid-contacting section of material which is compatible with and corrosion resistant to the fluid, which can be a body of magnetic material within a titanium enclosure or a body of chrome-molybdenum-iron alloy. The check valve and inlet are so arranged that the pump displacement can be reduced without reducing the bubble pumping capability of the pump. |
| WO 98/19627<br>May 14, 1998<br>Van Antwerp et al. | A medication infusion pump is provided for use in the delivery of a selected medication to a patient, wherein the pump includes internal surface coatings defining protein stable surfaces. In accordance with the invention, hydrophilic internal surface and related coating methods are provided to reduce or eliminate accumulation of medication deposits which can otherwise occur when handling complex protein-based medication. Preferred hydrophilic pump surfaces include hydrophilic surfactant (PEO) or (PEG) coatings which exhibit very low protein adsorption characteristics. Several methods are disclosed for producing such coatings, including direct surface modification, covalent and non-covalent attachment of polymers, and covalent attachment through a saline primer. |

Operation of these pumps may be effected by a combination of flow resistance within a fluid path and a characteristic known as "compliance". Flow resistance is related to how much pressure is required to make a desired quantity of fluid flow through the path in a given time period. Compliance is related to how a fluid path, as defined by the structural body forming the path or a part of the path, expands, contracts or deflects under an environmental input, such as, for example, a pressure load from a pulse stroke from an infusion pump mechanism that is intended to deliver an amount of medication to a catheter.

If a particular flow path (e.g. path from pump mechanism output port to distal end of a catheter) has little or no compliance, any attempt to move fluid into the flow path (e.g. at the pump mechanism output port) will only occur to the extent that substantially an equivalent amount of fluid will be moved out of the flow path (e.g. out of the distal end of the catheter). On the other hand, if a flow path offers a large amount of compliance, a fluid may be easily pushed into one end of the flow path, during a specified time period, with little or no fluid exiting the other end of the flow path during that time period.

In some pump designs too little compliance may influence the infusion pump's performance by offering increased resistance of flow at the inlet of the flow path (e.g. output port of the pump mechanism). If a significant amount of resistance is offered, the infusion pump mechanism may deliver less fluid, than predicted, for each pump stroke. It is further known that excessive compliance may influence the infusion pump mechanism's performance by offering insufficient resistance to flow at the inlet of the flow path (e.g. output port of the pump mechanism). If an insufficient amount of resistance is offered, it may result in delivery of more fluid, than predicted, with each stroke. Either situation may provide incorrect dosing of the fluid, which may have long term and short term health effects for a patient being treated by the fluid.

In some pump designs, especially with implantable pumps, low power consumption is of importance so that battery life is not prematurely reduced below an acceptable level and that useful life of the pump is of reasonable length. In electromagnetic pumps, such as those described in U.S. Pat. No. 5,797,733, as referenced in Table 1, it is desirable that the electromagnetic coil be activated for only for a short period of time, with only a limited amount of power so as to minimize battery drain. However, if an inappropriate amount of compliance exists, a piston that is used to force fluid from a fluid reservoir may not travel an intended length and thus may not cause a desired amount of material to be dispensed.

In the '733 patent, as illustrated in FIG. 4 of this referenced patent, it is proposed that an accumulator 436 form a portion of the flow path between the outlet tube 430 of the pump 420 and the catheter 440. It is proposed that this accumulator be in the form of a small compliant element. It is indicated that the accumulator 436 can comprise a small length of Silicone rubber tubing, i.e. about ½ inch in length and 1/32 inch inner diameter.

Among other things, the '733 patent further indicates that

" . . . a small accumulator is provided downstream of the pump outlet orifice large enough to contain the pulse volume of the pump with a reasonable pressure rise. The catheter diameter may then be small enough to ensure that the flow through the accumulator catheter combination is critically damped and no flow oscillations occur which might otherwise draw additional flow through the pump check valves. It is desirable that the accumulator be small enough so that a significant pressure rise occurs during the pump stroke. The back pressure build-up serves the purpose of preventing a large pulse volume when the supply pressure exceeds the delivery pressure."

However, even with some recognition of a need for an appropriate amount of compliance in the pump system, a need continues to exist in the art for improved methods of and apparatus for supplying compliance within infusion pump systems and particularly within implantable systems.

The use of silicone as a source of compliance within a fluid path, and especially for long term use, has many shortcomings: (1) It is subject to swelling, leakage, and change of mechanical properties, as it is permeable to water, air, and various other substances, such as preservatives that may be used with various types of insulin; (2) The compliance of silicone is based on its flexibility as opposed to its compressibility; (3) It is a hydrophobic material can aggravate physical instability of some drugs, e.g. insulin, which can lead to precipitation and build up of the drug within the system; (4) If exposed to body fluids, hard tissue may build up on the tubing to reduce its compliance with the progression of time; (5) If exposed to ambient pressure within the body, unintentional discharge of fluid may occur as a result of an impact, other significant pressure increase, or shock to the source of compliance; (6) If used within a portion of the system subject to high pressure flushing, the silicone may rupture.

SUMMARY OF THE DISCLOSURE

In view of the shortcomings noted above, it is a first object of the present invention to provide a source of compliance that is not permeable to fluids that it may come into contact with.

It is a second object of the present invention to provide a source of compliance that is compressible.

It is a third object of the invention to provide a source of compliance that is less likely to cause physical instability of the drugs that it will come into contact with, e.g. insulin.

It is a fourth object of the invention to provide a source of compliance that is less variable with the passage of time.

It is a fifth object of the invention to provide a source of compliance that is less likely to cause unintentional discharge of fluid into the body of a patient.

It is a sixth object of the invention to provide a source of compliance that is not subject to damage as a result of exposure to high pressures that might occur, for example, during a flushing operation, or the like.

It is intended that each of the above noted objects of the invention, as well as any other objects of the invention set forth explicitly or implicitly herein, be pursued alone, or in various combinations, by different aspects of the invention. It is further intended that additional objects of the invention provide infusion pumps that pursue or address one or more of the above noted objects of the invention alone or various combinations.

A first aspect of the invention provides an infusion pump for delivering a fluid to the body of a patient, including: (1) a pumping mechanism having a fluid entrance port and fluid exit port for transferring fluid from the entrance port to the exit port, (2) a reservoir for containing the fluid, the reservoir connected to the entrance port of the pumping mechanism by a first fluid path, (3) an outlet connected to the exit port of the pumping mechanism along a second fluid path for supplying fluid from the reservoir to the body of a patient, (4) a control device for controllably operating the pumping mechanism, (5) a source of compliance in communication with fluid along the first or second fluid paths for providing a source of compliance for fluid in proximity to the entrance port of the pump mechanism or for fluid exiting the exit port of the pumping mechanism, respectively. The source of compliance includes a structure selected from the group of (a) a compressible structure, (b) an expandable structure, (c) a non-permeable structure, and (d) a structure located within a flow path defined by a substantially non-compliant material.

A second aspect of the invention a method for infusing a fluid into a body of a patient, including: (1) providing fluid to a reservoir within an infusion device, (2) controlling a pumping mechanism having a fluid entrance port and fluid exit port for transferring fluid from the entrance port to the exit port, (3) directing a fluid from the reservoir to the entrance port of the pumping mechanism along a first fluid path, (4) directing fluid to an outlet connected to the exit port of the pumping mechanism along a second fluid path for supplying to the body of a patient, (5) operating the pumping mechanism in a controlled manner, (6) supplying a source of compliance in communication with fluid along the first or second fluid paths for providing a source of compliance for fluid in proximity of the entrance port of the pump mechanism or for fluid exiting the exit port of the pumping mechanism, respectively. The source of compliance includes a structure selected from the group of (a) a compressible structure, (b) an expandable structure, (c) a non-permeable structure, and (d) a structure located within a flow path defined by a substantially non-compliant material.

A third aspect of the invention provides an infusion pump for delivering a fluid to the body of a patient, including: (1) a pumping means having a fluid entrance port and fluid exit port for transferring fluid from the entrance port to the exit port, (2) a means for containing a fluid to be dispensed connected to the entrance port of the pumping means by a first fluid path, (3) an outlet means connected to the exit port of the pumping mechanism along a second fluid path for supplying fluid from the reservoir to the body of a patient, (4) a means for controllably operating the pumping mechanism, (5) a compliance means in communication with fluid along the first or second fluid paths for providing a source of compliance for fluid in proximity to the entrance port of the pump mechanism or for fluid exiting the exit port of the pumping mechanism, respectively. The compliance means includes a structure selected from the group of (a) a compressible structure, (b) an expandable structure, (c) a non-permeable structure, and (d) a structure located within a flow path defined by a substantially non-compliant material.

A fourth aspect of the inventions provides a compliance mechanism for use with a pump mechanism in an infusion pump that is intended to deliver a predetermined amount of fluid through an outlet from operation of the pump mechanism. The compliance mechanism includes at least one pillow. The at least one pillow includes a pair of diaphragms that are hermetically sealed to enclose a known volume of a gas or other compressible substance. The at least one pillow is positioned to be in fluid communication with fluid in the infusion pump.

A fifth aspect of the invention a compliance mechanism for use with a pump mechanism in an infusion pump that is intended to deliver a predetermined amount of fluid through an outlet from operation of the pump mechanism. The compliance mechanism includes a drum member including a pair of diaphragms that are hermetically sealed to open ends of a stand off member.

The drum encloses a trapped volume of gas or other compressible substance and is positioned to be in fluid communication with the fluid in the infusion pump.

A sixth aspect of the invention provides a compliance mechanism for use with a pump mechanism in an infusion pump that is intended to deliver a predetermined amount of fluid through an outlet from operation of the pump mechanism. The compliance mechanism includes (1) at least one diaphragm, and (2) a body having a cavity with at least one opening, wherein the at least one diaphragm is hermetically sealed to close off the at least one opening in the cavity. The diaphragm is positioned to be in fluid communication with the fluid in the infusion pump.

A seventh aspect of the invention provides an infusion pump for delivering a fluid to the body of a patient, including: (1) a reservoir for containing a fluid to be dispensed, (2) an outlet for supplying fluid from the reservoir to the body of a patient, (3) a pumping mechanism for transferring fluid from the reservoir to the outlet (4) a programmable control device, including an electrical circuit, for controllably operating the pumping mechanism, and (5) a compressible structure in communication with fluid in the infusion pump for providing a source of compliance within the infusion pump.

While certain aspects of the invention have been noted above, other aspects will be apparent to those of skill in the art upon study of the teachings herein. As noted above, it is not intended that each aspect of the invention simultaneously address all of the objectives set forth above. Each aspect of the invention may address a single one of the objectives or alternatively may address a combination of two or more objectives.

Some preferred embodiments provide implantable infusion pumps with sources of compliance positioned between an exit port of a pumping mechanism and an outlet (e.g. an opening in a catheter) of the infusion pump. Other embodiments provide compliance for fluid in an entrance port of the pumping mechanism. Insertion of compliance in a flow path that is down stream of the pumping mechanism may aid in minimizing negative effects associated with attempting to force fluid through a restricted flow path that is further down-stream, such as that offered by a catheter or other outlet component. Insertion of compliance before the pumping mechanism may aid in reducing negative effects associated with an up stream restricted flow path, such as that which might be offered by a rigid filter located between the reservoir and the pumping mechanism. Several structural components, assemblies, or configurations are used as sources of compliance. For example, compressible structures (e.g. pillows, drums) are used within a side port of the infusion pump. The compressible structures may quickly distort to accommodate for a large impulse of fluid into the flow path that can not otherwise be readily dealt with. The compression, in turn, results in a restoring force being exerted that returns the structure substantially to its original volume so as to slowly force fluid from the flow path.

Thus, some embodiments of the present invention provide an attachable, field replaceable catheter assembly with controlled compliance characteristics for use with an implantable infusion pump that attempts to deliver an amount of fluid in a short time period. However, to minimize energy consumption, it is typically desired to operate the pumping mechanism over a time period that is significantly less than that necessary to delivery a desired volume of fluid from an outlet of the infusion pump. The supplied compliance aids in ensuring that a desired amount of fluid is deliver for each operation of the pumping mechanism (e.g. each stroke of an electromagnetically driven piston).

According to one embodiment of the invention, a compliance mechanism is used with a pump mechanism in an infusion pump to aid in delivering a desired or predetermined amount of fluid through a catheter. The compliance mechanism includes a plurality of diaphragms used in the formation of at least one pillow. Each of the at least one pillows is formed from a pair of diaphragms that are hermetically sealed to enclose a known volume of a gas. The at least one pillow is preferably located within a fluid path that is separated from an exit port of the pump mechanism by a small amount of flow impedance, or resistance, so as to minimize the effects of flow resistance in the catheter.

In some embodiments, the compliance mechanism includes a support component to protect the at least one pillow from collapse beyond its structural limits during the pump stroke or during a flush out operation. Further embodiments provide pillows which can accommodate pressures up to about −8 to about 300 psi. Still further embodiments, form the diaphragms from a metallic material, such as titanium or the like, a metallic composite, or Halar film.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures:

FIG. 1 is a perspective view illustrating an implantable medication infusion pump equipped with a side port assembly;

FIG. 2 is a fragmented exploded perspective view depicting connection of the side port assembly onto the implantable infusion pump;

FIG. 3(a) is a top plan view of an attachable field replaceable side port/catheter assembly.

FIG. 3(b) is a cross-sectional view of the attachable field replaceable side port/catheter assembly as shown in FIG. 3(a).

FIG. 11(a) is a perspective view of a compliance mechanism in accordance with still another embodiment of the present invention.

FIG. 11(b) is an exploded perspective view of the components forming the compliance mechanism of FIG. 11(a).

FIG. 13 shows a partial cross-sectional view of a compliance mechanism in accordance with another embodiment of the present invention.

FIG. 14 shows a partial cross-sectional view of a compliance mechanism in accordance with yet another embodiment of the present invention.

DETAILED DESCRIPTION OF THE PREFERRED EMBODIMENTS

Figure 4:
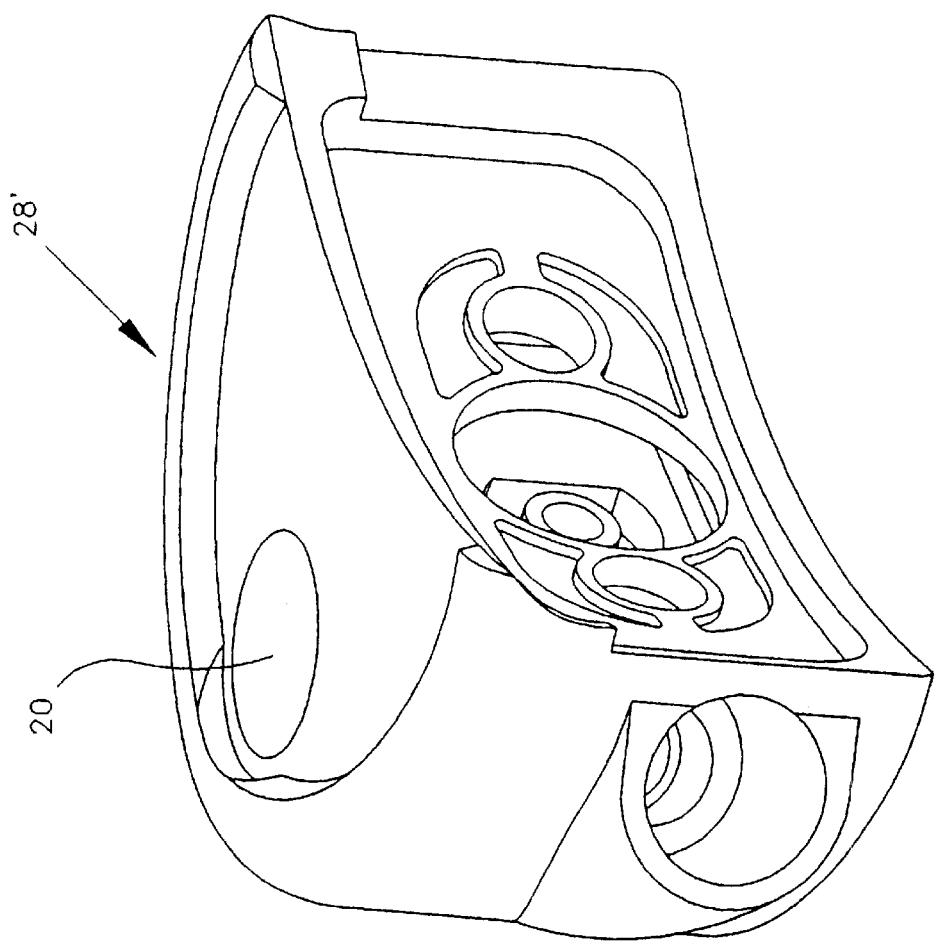
FIG. 4 is a side perspective view of a side port as shown in FIGS. 3(a) and 3(b).

According to some preferred embodiments of the invention, an implantable infusion pump is provided that includes a number of functionally related elements or assemblies: (1) an outer shell or housing, (2) a fluid reservoir located entirely within or forming part of the housing, (3) an inlet orifice functionally connected to the reservoir for allowing fluid to be supplied from outside the housing to the reservoir for filling the reservoir when the fluid supply gets low or is depleted, (4) a pumping mechanism, located entirely within or forming part of the housing, transfers fluid from an entrance port of the mechanism to an exit port of the mechanism, (5) a fluid flow path connecting the reservoir to the entrance port for a pumping mechanism, (6) an outlet that has an opening for dispensing fluid from the infusion pump to a desired location within the body of a patient, (7) a fluid flow path connecting the exit port to the outlet, (8) a mechanism and/or circuit for controlling the operation of the pumping mechanism to controllably dispense fluid from the infusion pump to the body of the patient. Filters may be included at any of various locations in the system, for example, between the inlet and the reservoir and/or between the reservoir and the entrance port of the pumping mechanism, and/or between the exit port of the mechanism and the outlet of the system.

The entrance port of the pump mechanism and exit port of the pump mechanism may be located within the mechanism assembly as opposed to defining an inlet or outlet of the assembly itself. The exit port of the mechanism is located at position within the fluid path for which the fluid has been acted on by the pumping mechanism to place it down-stream of the active part of the mechanism. The exit port may be defined by a check valve that allows fluid to leave the active portion of the mechanism on it down-stream path to the pump outlet but will not allow fluid flow in the reverse direction. The entrance port of the mechanism is located at a position within the fluid path for which fluid located up-stream of the position has not yet been acted upon or is in position set be forced through the exit port during a next operation of the mechanism. In the case of a piston pump, fluid located up-stream of the piston may be considered to have not yet reached the entrance port.

A fluid region may be considered to be in proximity to another fluid region (regardless of spatial separation) when a relatively small impedance exists in the flow path that connects the two regions. A relative small impedance may in turn be considered that which allows a desired amount (e.g. 50%–200% of the desired pump volume, more preferably 100%) to be transferred during a period of time (e.g. the time associated with pumping) between the two regions when experiencing a pressure no greater than the peak pressure induced in the fluid in the pump mechanism during pumping. A fluid region may be considered removed from another fluid region (regardless of spatial separation) when relatively large flow impedance exists between the two regions. The relatively large impedance may be considered anything greater than the relative small impedance. Alternatively, the relatively large impedance may be considered an amount that is at least two, five or even ten times larger than the relatively small impedance.

In some embodiments an infusion pump may include a main pump body with an attached side port and catheter. FIGS. 1 and 2 provide an overview of such an infusion pump. As illustrated, an implantable fluid infusion pump 10 comprises a substantially sealed housing 12 encasing a fluid storage reservoir 14 and an appropriate pump mechanism 16 for delivering discrete doses of a selected fluid through a catheter 18 to a patient. Catheter 18 may be fitted through shell 30 by a strain relief fitting 40. The pump 10 is equipped with a discharge side access port 20 which can be used to flush or clean accumulated particle-like residues from the catheter 18, and/or from internal pump flow passages. The pump housing 12 comprises a hermetically sealed case formed from a biocompatible material, such as titanium or titanium alloy. A primary inlet or refill port 22 is provided on the pump housing 12 to receive a hypodermic needle 24 to permit transcutaneous refilling of the medication storage reservoir 14 within the pump housing. During normal operation, the pump mechanism 16 within the housing 12 is programmably operated by an appropriate control circuit 26 to deliver the medication via the catheter 18 in accordance with individual patient requirements.

Over a period of time, particle-like deposits form the fluid can accumulate within the catheter 18, and also within internal flow passages of the pump 10. These medication deposits are believed to consist primarily of protein and other organic constituents, particularly when relatively complex and/or protein-based medications such as insulin are used. These accumulated deposits can eventually interfere with accurate pump operation and, in some instances, occlude the catheter 18.

A compact side port assembly 28 may be provided and may include discharge side access port 20. This side access port 20 permits facilitated flushing of particle-like deposits from the catheter 18. In addition, the side access port 20 can be used in combination with the primary refill port 22 to flush and clean residue from internal pump flow passages.

As shown, the side port assembly 28 comprises a relatively small, substantially half-circle case, body, or shell 30 adapted for facilitated interconnection between a pump mechanism exit port 32 and the catheter 18. Body 30 may be formed from a plastic or other material that is substantially non-compliant. As shown, the pump mechanism exit port 32 includes a discharge tube 34 which projects outwardly a short distance from one edge of the pump housing 12, and disposed within a generally cylindrical mounting lug 36 having a flanged end 38. The side port assembly has an inboard side or face adapted for flush-fit mounting against the side edge of the pump housing 12. A fitting and seal members provide sealed engagement between the discharge tube 34 and the side port. When the side port is fitted to the housing and engaged with the discharge tube an open slot in the housing shell 30 is aligned generally with the mounting lug 36, at a location behind the flanged end 38. A fork-shaped lock clip 42 includes a pair of generally parallel legs 44 for slide-fit reception through a slot in body 30 behind the flange lug end 38, for locking the side port assembly onto the pump housing 12.

A more detailed description of the overall construction and operation of implantable infusion pumps of the general type described above is provided in previously referenced U.S. Pat. Nos. 5,527,307; 4,373,527; and 4,573,994.

In the case of an external pumping device, as contemplated by some preferred embodiments, an inlet for refilling the reservoir and a reusable reservoir may be replaced by a disposal and replaceable reservoir that functionally connects to the pumping mechanism.

According to some preferred embodiments, the process utilized in supplying the desired fluid to the body of the patient includes a number of acts: (1) providing fluid to a reservoir within an infusion device, (2) directing fluid from the reservoir to an entrance port of a pumping mechanism along a first fluid path, (3) controlling a pumping mechanism to transfer fluid from a an entrance port of the mechanism to an exit port of the mechanism, (4) directing fluid, along a second fluid path, from the exit port of the mechanism to an outlet that releases the fluid into the body of the patient.

As shown in some of the drawings, a preferred embodiment of the invention locates one or more sources of compliance in an improved side port assembly that includes an attachable, field replaceable catheter for use with a high impulse-type delivery pump mechanisms (e.g. a mechanism that transfers fluid from an entrance port to an exit port by movement of a piston that is driven by a magnetic force from an electromagnet). As noted above, some preferred embodiments of the invention involve implantable infusion pumps that are placed inside the human body. Still, as noted above, further embodiments may be used with other types of infusion pumps, such as external pumps or the like, which may benefit from use of controlled compliance due to interaction between the infusion pump and the catheter.

Additionally, some preferred embodiments of the side pump/catheter assembly provide adequate protection from pressure extremes that may occur from changes in altitude, manufacturing testing, flushing, refilling, purging, and cleaning, or the like.

A preferred side port/catheter assembly 28' includes a body portion 30, a catheter 18, a strain relief fitting 40, a side port to housing seal 54, a locking clip 42, a filter assembly 56, and a valve/catheter interface assembly 58 (that can close the catheter inlet when the catheter is removed from the side port) as shown in FIGS. 3(a) and 3(b). As indicated in 3(b) the catheter may be removable from the side port with a valve closing the side port when the Because of the fluid restriction offered by the catheter portion 18 (including the diameter of the lumen and the catheter length), it has been found that a compliance control device is more preferably located between the exit port of pump mechanism and the catheter portion 18 of the side port/catheter assembly 28'. Preferred locations are shown as those between points 50 and 52 of FIG. 3(b). However, in alternative embodiments, other suitable locations may be used. As it is intended that a desired amount of fluid be driven out of the exit port of the pump mechanism, the choice for placement and quantity of compliance is dependent on several factors: (1) the available, or desired, pumping force that is exerted on the fluid by the mechanism, (2) the desired duration of pumping, and (3) the impedance of the flow path between the exit port of the mechanism and the outlet of the system. The location and amount of compliance preferably allows a full stroke of fluid to be released from the pump mechanism to the exit port without excess electrical power consumption. It is known that the shorter the electrical impulse supplied to an electromagnetically driven pump mechanism the less drain on the power supply. Thus, if appropriate system compliance is present, minimal power consumption can be achieved while still delivering a desired amount of fluid in a desired amount of time. The compliance should be sufficiently large to allow the pump mechanism to transfer an appropriate amount of fluid without fighting unproductive back pressure while having compliance low enough that it offers sufficient force to drive stored liquid from the fluid path beyond the exit port out of the output orifice between successive pulse operations.

Figure 5:
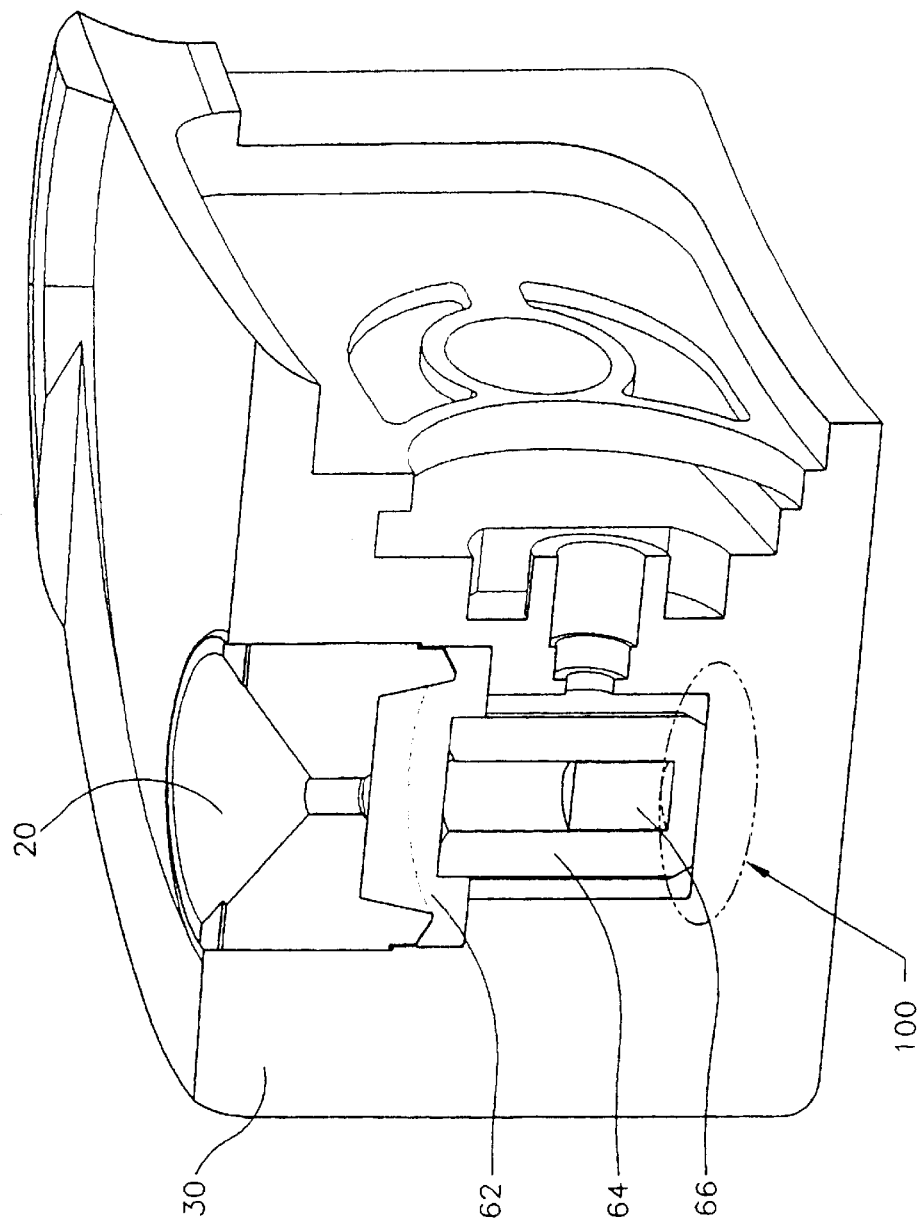
FIG. 5 is a perspective cross-sectional view of the side port, as shown in FIG. 4, showing one proposed site for the improved compliance mechanism.

In some preferred embodiments, a compliance mechanism 100 is located below side access port 20, below septum 62, and filter 64, as well as below a spacer element 66 between the filter 14 and body 30, as indicated in FIG. 5.

Figure 6A:
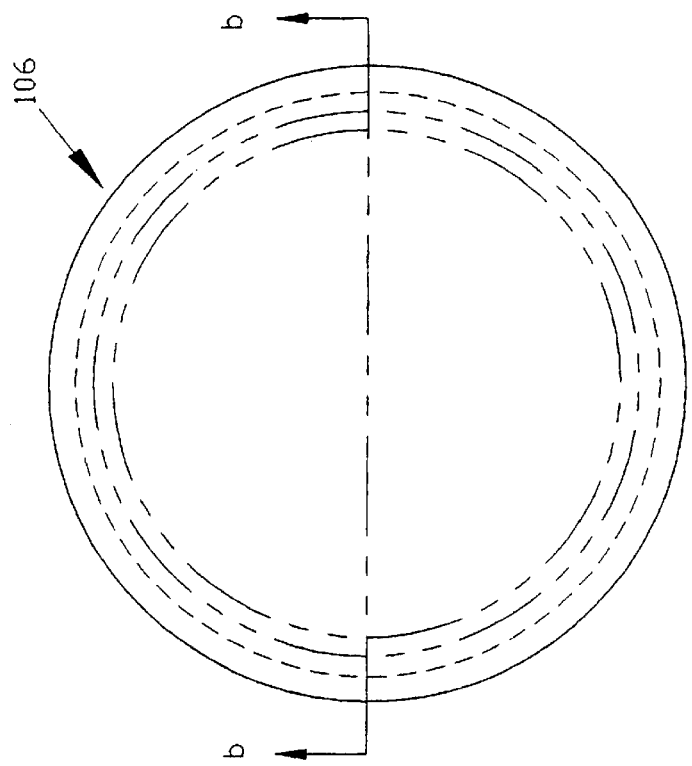
FIG. 6(a) is a top perspective view of a pillow for use as a compliance mechanism in accordance with an embodiment of the present invention.
Figure 6B:
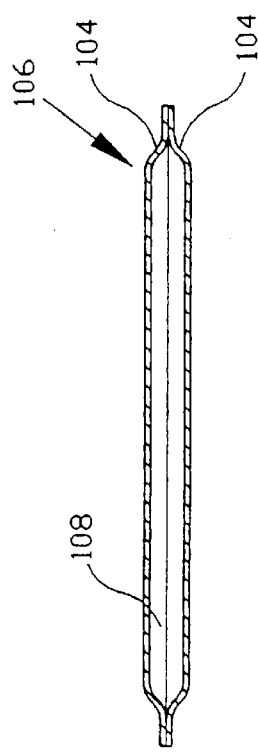
FIG. 6(b) is a perspective cross-sectional view of the pillow for use as the compliance mechanism as shown in FIG. 6(a).
Figure 7A:
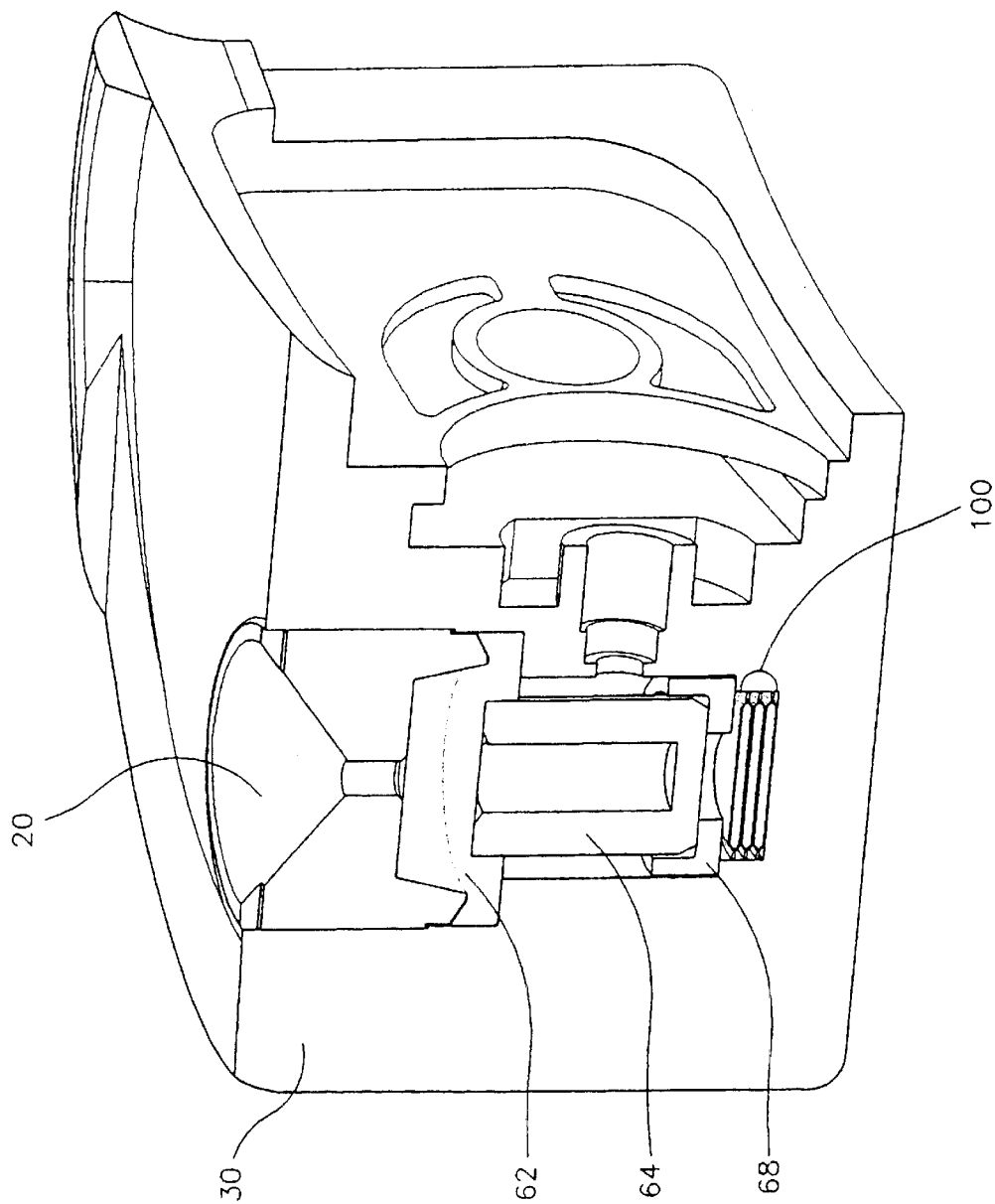
FIG. 7(a) is a perspective cross-sectional view of an attachable field replaceable side port/catheter assembly using a compliance mechanism in accordance with an embodiment of the present invention.
Figure 7B:
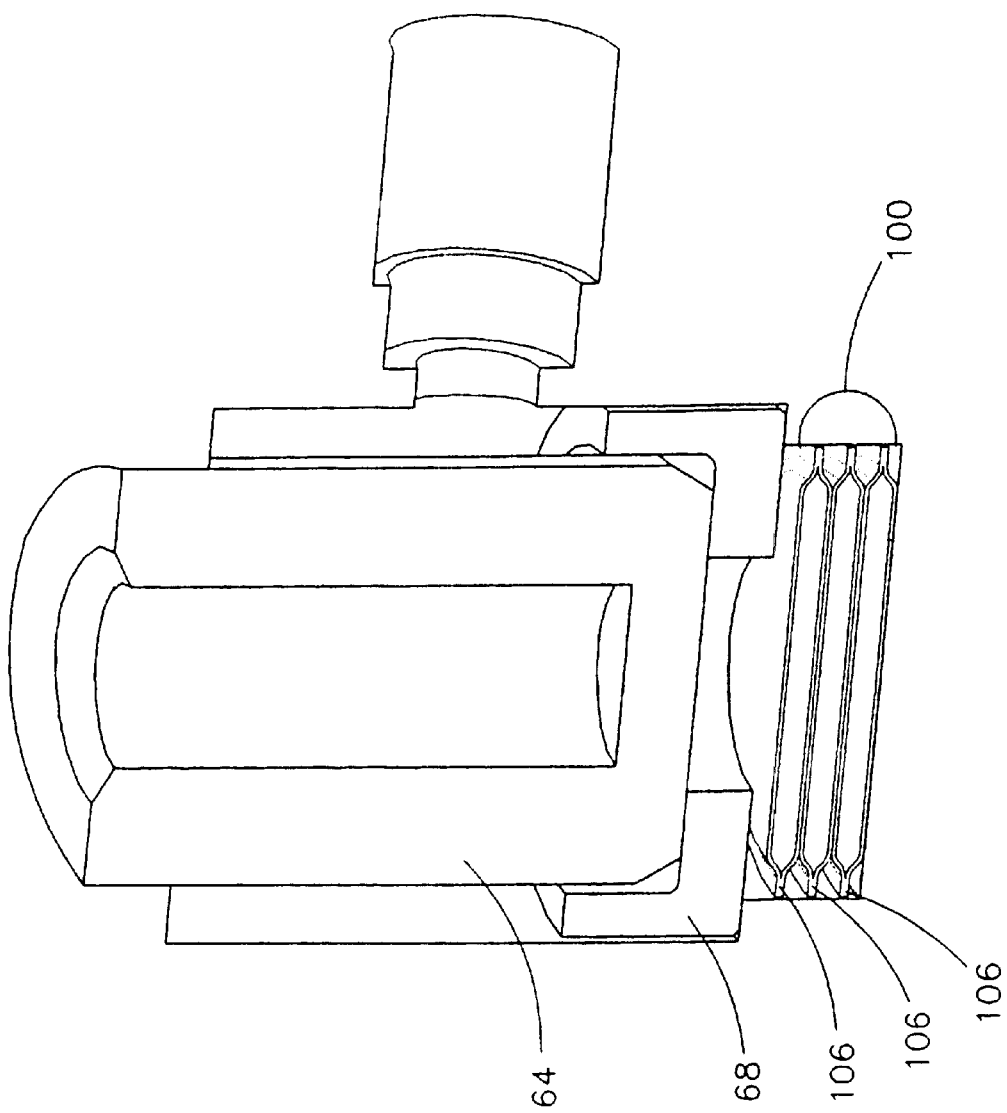
FIG. 7(b) is an enlarged perspective partial cross-sectional view of the compliance mechanism shown in FIG. 7(a).

A first preferred embodiment of a compliance mechanism 100, as shown in FIGS. 6–7, is a pillow assembly 106, that uses a plurality of diaphragms 104 coupled together to form gas filled pillows 106 or cushions, with predictable compliance properties within the implantable infusion pump environment. In preferred embodiments, the pillow assembly 106 uses diaphragms 104 as shown in FIG. 6 that hermetically encloses a volume, e.g. preferably known volume) of a known gas 108, such as air, Argon, Helium, Nitrogen, mixtures or pure gases, Freon (including Freon 113), or the like, between two diaphragms 104 that are welded and sealed together. The volume of gas 108 is preferably controlled such that at high pressure extremes the internal to external pressure equalization occurs at a condition which does not exceed elastic limit of the pillow or the yield strength of the chosen diaphragm material. In this way, the compliance mechanism 100 becomes self-supporting at high pressure extremes and does not collapse or degrade. In particular embodiments, the compliance mechanism 100 is formed from two or more pillows 106 (see FIG. 7) using the diaphragms 104, as shown in FIG. 6. In FIG. 7, filter 64 is held above the source of compliance by support 68. A spacer may be placed above the lower portion of filter 64 to prevent the filter or compliance members from being damaged by a hypodermic needle. In preferred embodiments, air is used since it has an increasing pressure curve as the pillow 106 and the diaphragms are compressed. However, Freon 113, or the like, may also be used to take advantage of its relatively linear or flat pressure curve, and the feature that upon full compression, the Freon 113 will become a liquid to prevent over compression of the pillows 106 and diaphragms 104 beyond the structural limits of the materials that they are formed from.

In some preferred embodiments, the diaphragms 104 are formed from a protein and bio-compatible material, such as titanium, titanium alloys, stainless steel, MP35N, Nitinol, or the like, that are hermetically joined together by a method such as TIG welding, laser welding or the like. Inclusion of appropriate trace materials, such as helium, helium radio-isotopes or the like, within the known volume of gas 108 during the welding process allows for easy detection and inspection of whether the diaphragms 104 are hermetically sealed after welding. In alternative embodiments, other suitable materials for the diaphragm 104 may be used, such as Halar Film (ethelyne-chlortriflouroethelyne copolymer (ECTFE)), plastic composites, laminates or the like may be used. In addition other methods of sealing the diaphragms 104 together may be used, such as adhesives, or the like. In some preferred embodiments, three pillows 106 are used to form the compliant member 100. However, in alternative embodiments, more or less pillows 106, or a bellows, may be used, with the selection being dependent on the characteristics of the implantable infusion pump mechanism and the compliance characteristics of the catheter portion 12 and catheter assembly 10.

In still further preferred embodiments the pillows, diaphragms, or other components forming the source of compliance may be supplied with a protein stabilized surface coating for those portions of the surface that will be in contact with the fluid (e.g. coating over a titanium substrate). Such coatings are described in WO 98/19627 and include such things as hydrophilic polymers, proteins, or polyurethane.

Figure 8B:
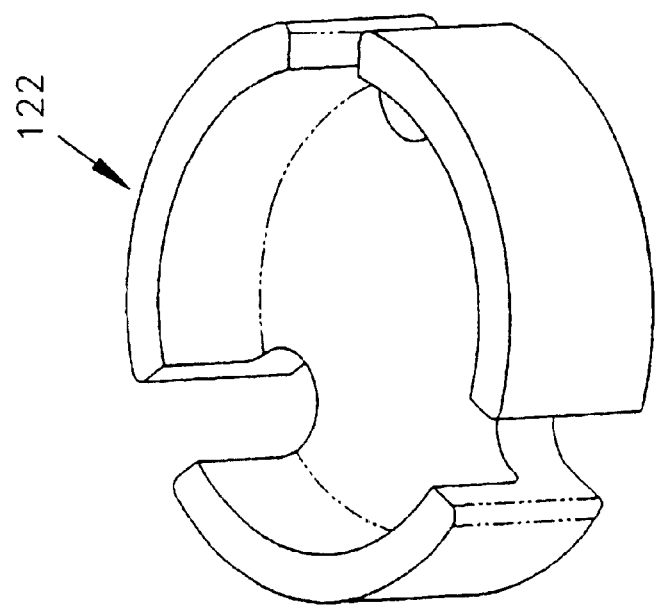
FIG. 8(b) is a perspective view of a peripheral flow support structure for use with a preferred embodiment of a compliance structure as show in FIGS. 7(a) and 7(b).
Figure 8A:
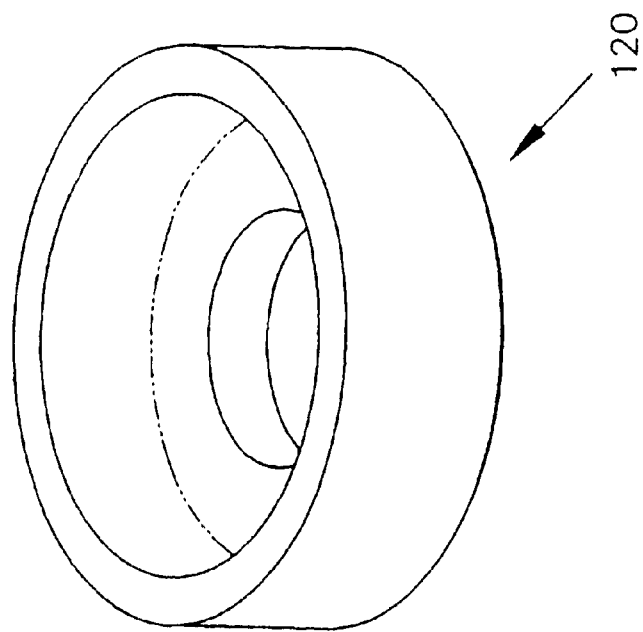
FIG. 8(a) is a perspective view of a central flow support structure for use with a preferred embodiment of the compliance structure as show in FIGS. 7(a) and 7(b).
Figure 9B:
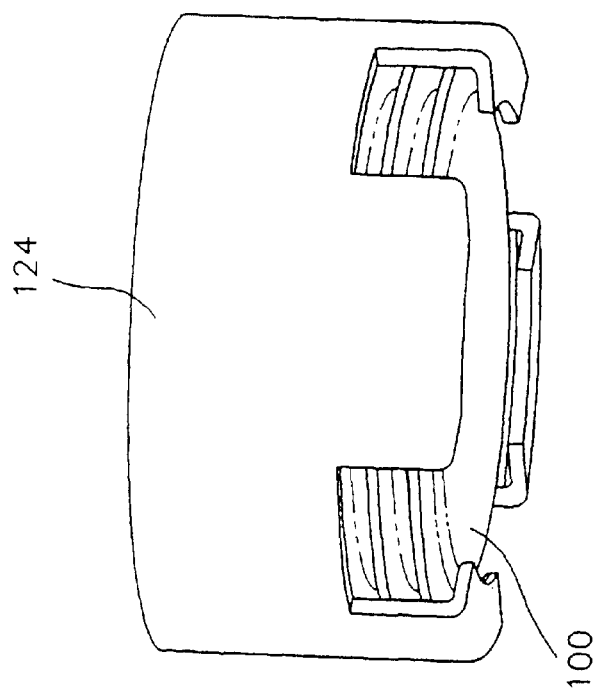
FIG. 9(b) is a perspective view of alternative support components that include the pillow assembly for another embodiment of the compliance mechanism shown in FIGS. 7(a) and 7(b).
Figure 9A:
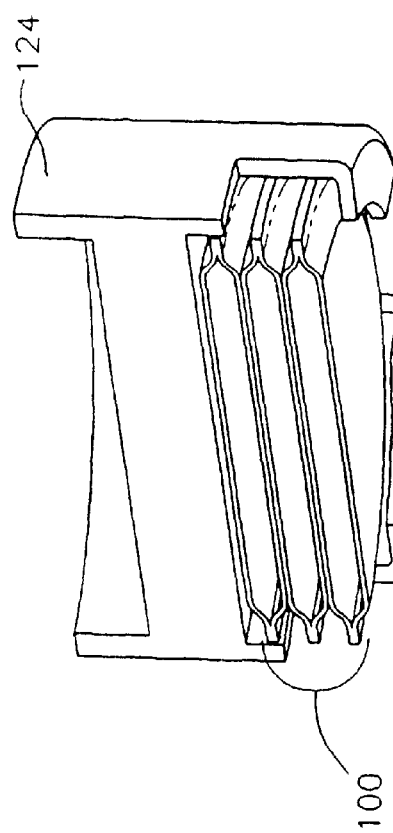
FIG. 9(a) is a perspective cross-sectional view of alternative support components that include the pillow assembly for another embodiment of the compliance mechanism shown in FIGS. 7(a) and 7(b).
Figure 10:
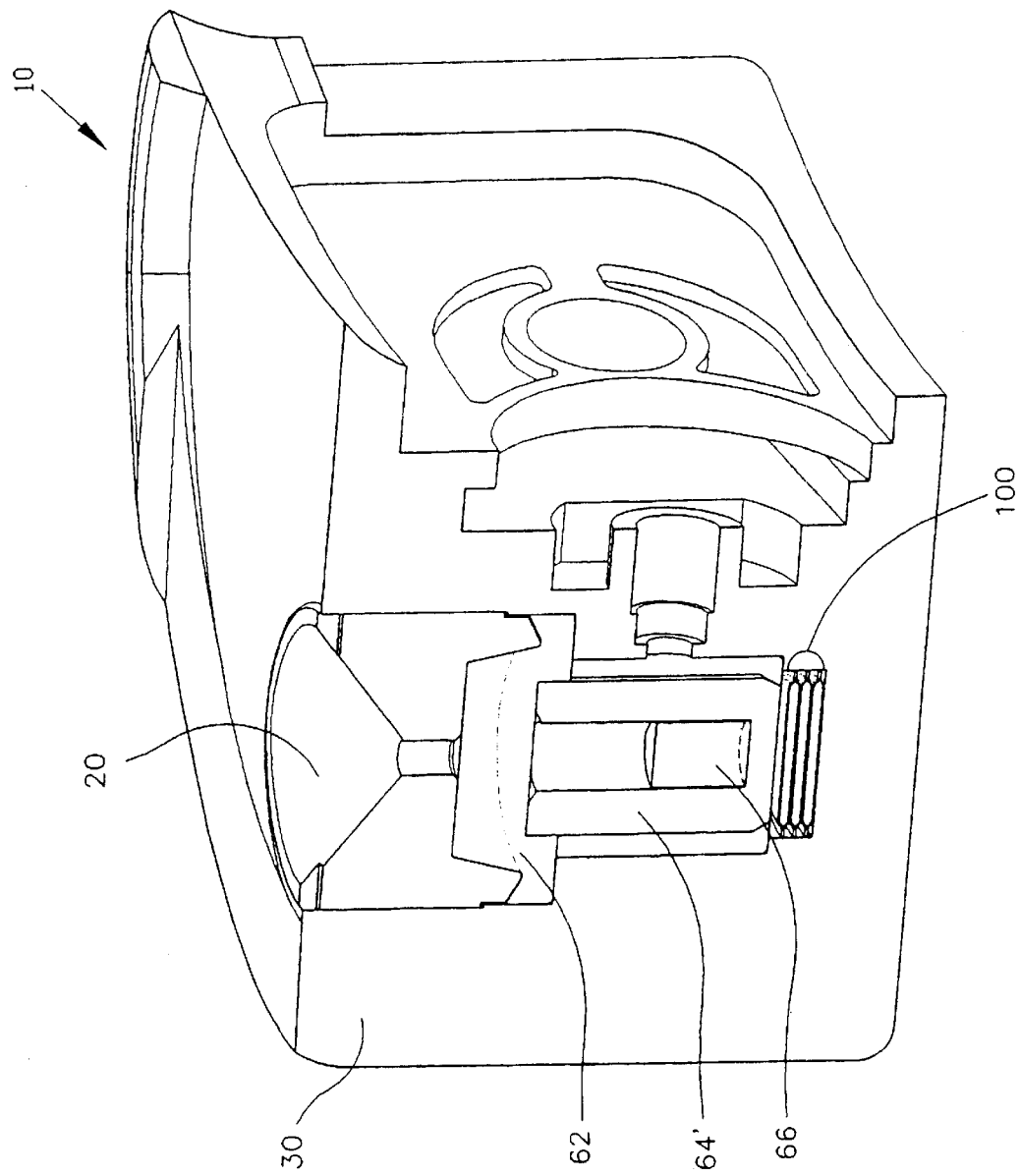
FIG. 10 is a perspective cross-sectional view of an attachable field replaceable side port assembly that utilizes a filter support component that integrates the filter and support functions with the compliance mechanism in accordance with another embodiment of the present invention.

Further embodiments of the compliance mechanism 100 in the assembly may require the addition of a structural "support" component such as central flow support 120 in FIG. 8(a), peripheral flow support 122 in FIG. 8(b) to facilitate reception and flow of the fluid received during each stroke of the infusion pump mechanism. As shown in FIGS. 9(a) and 9(b), the pillow assemblies 106 may also be included and formed in an interior recess or cavity in the support member 124. The use of supports may increase the life of the compliance mechanism 100. In other embodiments, the support member may be omitted and a hanging filter component 64' may include additional support structures 126, as shown in FIG. 10, to integrate the filter and support functions to retain the filter component 64' in position during pump strokes, cleaning, refilling, purging or the like.

Figure 12B:
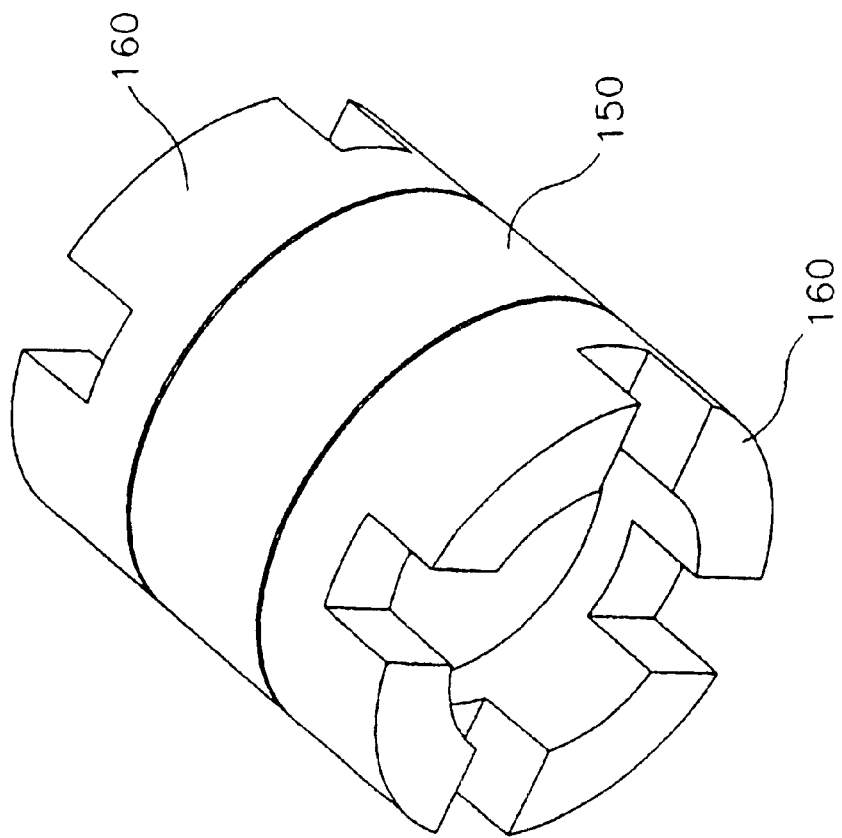
FIG. 12(b) is a perspective view of the compliance mechanism of FIG. 11(a) positioned between two support structures like those shown in FIG. 12(a).
Figure 12A:
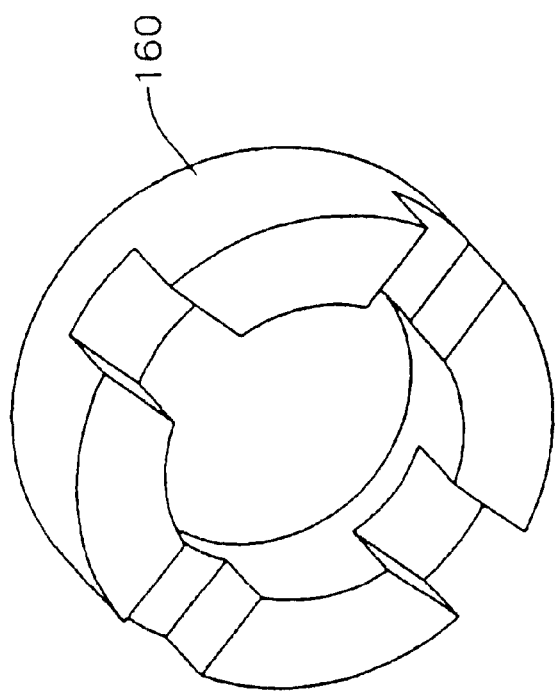
FIG. 12(a) is a perspective view of a support structure for use with the compliance mechanism of FIGS. 11(a) and 11(b).

A second embodiment of a compliance mechanism 150, as shown in FIG. 11, utilizes a drum assembly 152 with predictable compliance properties in the implantable infusion pump environment. The drum assembly 152 uses diaphragms 106, as described above in the first embodiment. This embodiment uses an internal spacer structure (e.g. over pressure star 154) within a stand off collar 156 between diaphragms 106 to provide support to the diaphragms during compression to substantially inhibit the compression of the diaphragms 106 beyond structural limits. In alternative embodiments, different shaped spacer structures 154 may be used, and the number of spacer structures 154 and diaphragms 106 may be increased. In alternative embodiments, the standoff collar may be omitted, if sufficient seal and structural support is provided by the body 30 of the implantable infusion pump. These embodiments may also use supports 160 to further enhance the durability of the compliance mechanisms, as shown in FIG. 12. Further alternatives may use a variation of the filter support shown in FIG. 10.

FIG. 13 shows a partial cross-sectional view of a compliance mechanism 200 in accordance with another embodiment of the present invention. The compliance mechanism 200 includes a channel 202 that extends to the exterior surface of the body 30. The exterior opening of the channel 202 is covered by a diaphragm 204 that provides sufficient deflection upon receipt of an impulse from the pump medication. In preferred embodiments, the diaphragm 204 may be made out of similar materials and have similar properties to the diaphragms 104 described above. Preferably, the diaphragm is welded, or attached by adhesives to the body 30. In alternative embodiments, other suitable materials, such as plastic, Halar, composites or the like may be used. In preferred embodiments, the fluid acts upon the diaphragm to cause deflection and the diaphragm is non-permeable to the fluid. However, in alternative embodiments, the compliance mechanism 200 may include an additional diaphragm (not shown) to close off the channel 202, and the enclosed space between the diaphragms may be filled with gases as described above. The enclosed area may be filled with a liquid, particularly when the lower surface of diaphragm 204 is adjacent to a volume of gas.

FIG. 14 shows a partial cross-sectional view of a compliance mechanism 300 in accordance with yet another embodiment of the present invention. . The compliance mechanism 300 includes a cavity 302 that does not extend to the exterior surface of the body 30. The cavity 302 has an opening at the support member 120 that is covered by a diaphragm 304 that provides sufficient deflection upon receipt of an impulse from the pump medication. In preferred embodiments, the diaphragm 304 may be made out of similar materials and have similar properties to the diaphragms 104 described above. Preferably, the diaphragm is welded, or attached by adhesives to the body 30. In alternative embodiments, other suitable materials, such as plastic, Halar, composites or the like may be used.

In other embodiments, the source of compliance may be located within the main enclosure of the infusion port as opposed to in a side port assembly.

In the previously discussed embodiments, the source of compliance was placed in position primarily to provide a space for fluid to occupy as a result of significant local pressure increases that may accompany the operation of a pumping mechanism. The pumping mechanism attempts to transfer or force a desired quantity of fluid from an entrance port of the pump mechanism to an exit port of the pump mechanism, in a short period of time (e.g. around 1.5 millisecond or less). Typically, the volume of fluid to be transferred is greater than what can be forced through the outlet of the system in the short time period, as such a pressure sensitive compliant device is used to provide a temporary storage location and a longer term fluid displacement force than provided by the pump mechanism. In this regard it is desired that the compliant assembly or member be able to operate elastically under pressures as high as about 300 psig. Of course, the actual pressure range and limit may be more or less than this value depending on system configuration and to what processes the source of compliance may be subjected.

In contrast to the previous embodiments where a pressure increase must be elastically accommodated by the source of compliance, other embodiments may require the source of compliance to operate elastically under decreases in pressure and thus to temporarily remove volume from a region of the flow path and to exert a long term force to pull fluid into the region. Such negative pressure (e.g. pressures below ambient) environments may temporarily occur in fluid regions that are up-stream of the entrance port of the pump mechanism. As the pump mechanism operates and transfers fluid from the entrance side to the exit side, the volume of fluid that is desired to be transferred may be greater than what can be transferred from the reservoir to the entrance port of the mechanism in the short period of time allowed (approximately 1.5 millisecond or less). The decreased pressure on the entrance side may be so great as to limit the ability of the pump mechanism to supply the desired amount of fluid. This is particularly true when a rigid, low flow filter, or other flow restrictor, separates the entrance port from the reservoir. If the source of compliance is to be utilized in such environments it is preferred that it be able to operate elastically within the pressure range that might be encountered (e.g. down to −8 psig).

As such, in certain embodiments it may be advantageous to place a source of controlled compliance in communication with a portion of the fluid path that is located up stream of the pump mechanism. In particular, it may be advantageous to place the source of compliance along the fluid path between the reservoir and an entrance port to the pumping mechanism. Even more particularly, the source of compliance may be located between a the entrance port of the pump mechanism and a rigid filter component that may be used to form a barrier over which a substantial pressure can built up during operation of the pumping mechanism.

In still further additional embodiments, the diaphragms 104 and pillow assembly 100 may be replaced with other resilient devices, such as elastic materials, foam, or the like, which provide compressibility or be deflectable particularly when they are of a material or coated with a material that is non-permeable to the fluid, fluids, or gases that they may come into contact with.

In some preferred embodiments as discussed above, the source of compliance preferably includes unitary structures or assemblies that are compressible, expandable, non-permeable to fluids encountered (e.g. gases or liquids), and/or are located within a flow path defined at least in part by a substantially non-compliant material. In some preferred embodiments the amount of compliance provided by the source of compliance may be within a range of about 10% to about 200%, more preferably between about 20% to about 130%, of the intended volume of fluid to be delivered by a single operation of the pump mechanism when experiencing a pressure in the range of 5 to 200 psig, more preferably between 10 to 100 psig. The relationship between compliant volume and pressure is more particularly based on an anticipated peak transient pressure exerted by the pump during pumping, length of time associated with pumping, that amount of impedance between the exit port of the pumping mechanism and the pump outlet, and the volume of fluid that is desired to be dispensed. Based on consideration of these issues, one of ordinary skill in the art may, at least, empirically determine an appropriate amount of compliance to add to a particular system. In some preferred embodiments a compliance of about 0.5 microliters at about 20 psig is considered appropriate when the desired pump volume is about 0.5 microliters. This amount of compliance, may for example, be offered by one or more pillows or drums (e.g. 2 or 3 pillows)

As noted above, if a catheter lumen is small and restrictive or if other restrictions exist in the flow path, an electromagnetic piston pump mechanism may not be able to push or pull the full stroke into the catheter or other restricted region in the very short time of piston action (e.g. of less than about 1.5 millisecond). To obviate the resulting problems in fluid delivery a controlled source of compliance is added to the system so that the fluid may be stored in the first millisecond and then made to flow under the lower force offered by the source of compliance during subsequent milliseconds.

While the description above refers to particular embodiments of the present invention, it will be understood that many modifications may be made without departing from the spirit thereof. The accompanying claims are intended to cover such modifications as would fall within the true scope and spirit of the present invention. For example, while examples of self contained controllable sources of compliance have been explicitly disclosed herein, other self contained sources of compliance will be apparent to those of skill in the art after reviewing the teachings herein. Alternative sources of compliance might have adjustable compliance, e.g. a source that includes a clamping mechanism that can change the effective compliance of the source by varying its maximum size volume.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion pump for delivering a fluid from a reservoir to a body of a patient, the infusion pump comprising:
    a pumping mechanism located along a fluid path for supplying fluid to the body of a patient; and
    a source of compliance located outside of the reservoir and in communication with fluid along said fluid path for providing a source of compliance for fluid in proximity to the pumping mechanism or for fluid exiting the pumping mechanism, wherein the source of compliance comprises a structure selected from the group of (a) a compressible structure, (b) an expandable structure, (c) a non-permeable structure, and (d) a structure located within a flow path defined by a substantially non-compliant material, wherein the structure is a hollow structure having an inside surface and an outside surface, and wherein, in use, the outside surface of the structure is in communication with the fluid in the fluid path and the inside surface is not in communication with the fluid in the fluid path.

2. The infusion pump of claim 1 additionally comprising an inlet for supplying fluid to a reservoir and wherein the infusion pump is implantable.

3. The infusion pump of claim 2 wherein an outlet of the fluid path is formed by an opening in a catheter that is implanted subcutaneously in the body of the patient.

4. The infusion pump of claim 3 wherein the catheter is implanted within the peritoneal cavity of the patient.

5. The infusion pump of claim 2 wherein the reservoir supplies fluid through a filter to an entrance port of the pumping mechanism.

6. The infusion pump of claim 1 wherein the source of compliance comprises a pillow structure that comprises a pair of diaphragms that are hermetically sealed to enclose a volume of a gas.

7. The infusion pump of claim 6, wherein the pillow can accommodate external pressures in the range of about –8 psi to about 300 psi.

8. The infusion pump of claim 6 wherein the diaphragms are formed from a material selected from the group consisting of metallic materials, metallic composites, and Halar films.

9. The infusion pump of claim 7 wherein the diaphragm comprises titanium.

10. The infusion pump of claim 8 wherein a surface of the diaphragm that is exposed to the fluid is substantially coated with a protein stable surface that comprises a hydrophilic substance.

11. The infusion pump of claim 2 wherein the amount of compliance provided is within a range of 10% to 200% of the intended volume of fluid to be delivered by a single operation of the pump mechanism within a range of 5 to 200 psig.

12. The infusion pump of claim 2 wherein the source of compliance comprises:

a pair of diaphragms; and
    a standoff member having two open ends;
    wherein the each diaphragm of the pair are hermetically sealed to respective open ends of the standoff member to enclose a volume of a gas and to form a drum structure.

13. The infusion pump of claim 12 wherein the drum structure additionally comprises a spacer member located within the standoff member between the pair of diaphragms.

14. The infusion pump of claim 2 wherein the source of compliance comprises:
    a body having a cavity with at least one opening;
    a diaphragm that is hermetically sealed to close off the at least one opening in the cavity; and
    wherein the diaphragm is in fluid communication with a desired portion of a fluid flow path.

15. An infusion pump according to claim 1, wherein the infusion pump further comprises:
    a reservoir for containing the fluid; and
    a control device for controllably operating the pumping mechanism;
    wherein the pumping mechanism has a fluid entrance port and a fluid exit port for transferring fluid from the entrance port to the exit port;
    wherein the reservoir is connected to the entrance port of the pumping mechanism by a first part of the fluid path; and
    wherein an outlet of the fluid path is connected to the exit port of the pumping mechanism by a second part of the fluid path for supplying fluid from the reservoir to the body of a patient.

16. An infusion pump according to claim 15, wherein the infusion pump further comprises an inlet for supplying fluid to the reservoir and wherein the infusion pump is implantable.

17. An infusion pump according to claim 16, wherein the reservoir supplies fluid through a filter to the entrance port of the pumping mechanism.

18. An infusion pump according to claim 1,
    wherein the pumping mechanism has a fluid entrance port and a fluid exit port for transferring fluid from the entrance port to the exit port; and
    wherein the source of compliance is located along the part of the fluid path that is between the exit port of the pumping mechanism and an outlet of the fluid path into the body.

19. A method for infusing a fluid from a reservoir into a body of a patient, comprising:
    directing fluid along a fluid path containing a pumping mechanism for supplying fluid to the body of a patient; and
    supplying a source of compliance located outside of the reservoir and in communication with fluid along said fluid path for providing a source of compliance for fluid in proximity to the pumping mechanism or for fluid exiting the pumping mechanism, wherein the source of compliance comprises a structure selected from the group of (a) a compressible structure, (b) an expandable structure, (c) a non-penneable structure, and (d) a structure located within a flow path defined by a substantially non-compliant material, wherein the structure is a hollow structure having an inside surface and an outside surface, and wherein, in use, the outside surface of the structure is in communication with the fluid in the fluid path and the inside surface is not in communication with the fluid in the fluid path.

20. A method for infusing a fluid into the body of a patient according to claim 19, wherein the method further comprises:

providing a fluid to a reservoir within an infusion device;

controlling the pumping mechanism having a fluid entrance port and a fluid exit port for transferring fluid from the entrance port to the exit port;

directing the fluid from the reservoir to the fluid entrance port along a first part of the fluid path; and operating the pumping mechanism in a controlled manner.

21. An infusion pump for delivering a fluid from a reservoir to a body of a patient, comprising:

a pumping means located along a fluid path for supplying fluid to the body of a patient; and a compliance means located outside the reservoir and in communication with fluid along said fluid path for providing a source of compliance for fluid in proximity to the pumping means or for fluid exiting the pumping means, wherein the compliance means comprises a structure selected from the group of (a) a compressible structure, (b) an expandable structure, (c) a non-permeable structure, and (d) a structure located within a flow path defined by a substantially non-compliant material, wherein the structure is a hollow structure having an inside surface and an outside surface, and wherein, in use, the outside surface of the structure is in communication with the fluid in the fluid path and the inside surface is not in communication with the fluid in the fluid path.

22. An infusion pump for delivering a fluid into the body of a patient according to claim 21, wherein the infusion pump further comprises:

a means for containing a fluid to be dispensed; and a means for controllably operating the pumping means;

wherein the pumping means has a fluid entrance port and a fluid exit port for transferring fluid from the entrance port to the exit port; and wherein the means for containing a fluid to be dispensed is connected to the fluid entrance port of the pumping means by a first part of the fluid path.

* * * * *